(12) United States Patent
Marchionni et al.

(10) Patent No.: US 8,394,761 B2
(45) Date of Patent: *Mar. 12, 2013

(54) METHODS FOR TREATING CONGESTIVE HEART FAILURE

(75) Inventors: Mark Marchionni, Arlington, MA (US); Ralph Kelly, Chestnut Hill, MA (US); Beverly Lorell, Needham, MA (US); Douglas B. Sawyer, Brookline, MA (US)

(73) Assignees: Beth Israel Deaconess Medical Center, Boston, MA (US); The Brigham and Women's Hospital, Inc., Boston, MA (US); Acorda Therapeutics, Inc., Ardsley, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/292,193

(22) Filed: Nov. 9, 2011

(65) Prior Publication Data

US 2012/0065130 A1 Mar. 15, 2012

Related U.S. Application Data

(60) Continuation of application No. 12/655,361, filed on Dec. 29, 2009, now Pat. No. 8,076,283, which is a division of application No. 10/646,268, filed on Aug. 22, 2003, now Pat. No. 7,662,772, which is a division of application No. 09/298,121, filed on Apr. 23, 1999, now Pat. No. 6,635,249.

(51) Int. Cl.
*A61K 38/18* (2006.01)

(52) U.S. Cl. .................................. 514/2; 514/8
(58) Field of Classification Search .................. None
See application file for complete search history.

(56) References Cited

U.S. PATENT DOCUMENTS

| | | |
|---|---|---|
| 3,773,919 A | 11/1973 | Boswell et al. |
| 4,179,337 A | 12/1979 | Davis et al. |
| 4,301,144 A | 11/1981 | Iwashita et al. |
| 4,485,045 A | 11/1984 | Regen |
| 4,496,689 A | 1/1985 | Mitra |
| 4,544,545 A | 10/1985 | Ryan et al. |
| 4,640,835 A | 2/1987 | Shimizu et al. |
| 4,670,417 A | 6/1987 | Iwasaki et al. |
| 4,791,192 A | 12/1988 | Nakagawa et al. |
| 5,367,060 A | 11/1994 | Vandlen et al. |
| 5,530,109 A | 6/1996 | Goodearl et al. |
| 5,641,869 A | 6/1997 | Vandlen et al. |
| 5,667,780 A | 9/1997 | Ho et al. |
| 5,714,385 A | 2/1998 | Mather et al. |
| 5,716,930 A | 2/1998 | Goodearl et al. |
| 5,721,139 A | 2/1998 | Mather et al. |
| 5,834,229 A | 11/1998 | Vandlen et al. |
| 5,840,525 A | 11/1998 | Vandlen et al. |
| 5,856,110 A | 1/1999 | Vandlen et al. |
| 5,859,206 A | 1/1999 | Vandlen et al. |
| 5,968,511 A | 10/1999 | Akita et al. |
| 6,033,660 A | 3/2000 | Mather et al. |
| 6,087,323 A | 7/2000 | Gwynne et al. |
| 6,096,873 A | 8/2000 | Schaefer et al. |
| 6,121,415 A | 9/2000 | Godowski et al. |
| 6,136,558 A | 10/2000 | Ballinger et al. |
| 6,156,728 A | 12/2000 | Gao |
| 6,162,641 A | 12/2000 | Goldman et al. |
| 6,169,070 B1 | 1/2001 | Chen et al. |
| 6,252,051 B1 | 6/2001 | Godowski et al. |
| 6,387,638 B1 | 5/2002 | Ballinger et al. |
| 6,399,746 B1 | 6/2002 | Vandlen et al. |
| 6,444,642 B1 | 9/2002 | Sklar et al. |
| 6,446,242 B1 | 9/2002 | Lien et al. |
| 6,593,290 B1 | 7/2003 | Gao |
| 6,635,249 B1 * | 10/2003 | Marchionni et al. ........ 424/145.1 |
| 6,750,196 B1 | 6/2004 | Reh et al. |
| 7,037,888 B1 | 5/2006 | Sklar et al. |
| 7,226,907 B1 | 6/2007 | Zhou |
| 7,662,772 B2 * | 2/2010 | Marchionni et al. ........... 514/1.1 |
| 8,076,283 B2 * | 12/2011 | Marchionni et al. ........... 514/9.6 |

FOREIGN PATENT DOCUMENTS

| | | |
|---|---|---|
| AU | 6827894 B | 12/1994 |
| DE | 3218121 A1 | 11/1983 |
| EP | 0036676 A1 | 9/1981 |
| EP | 0052322 A2 | 5/1982 |
| EP | 0058481 A1 | 8/1982 |
| EP | 0088046 A2 | 9/1983 |
| EP | 0102324 A2 | 3/1984 |
| EP | 0133988 A2 | 3/1985 |
| EP | 0142641 A2 | 5/1985 |
| EP | 0143949 A1 | 6/1985 |
| EP | 0647449 A1 | 4/1995 |
| JP | 58118008 A | 7/1983 |
| WO | WO-8901489 A1 | 2/1989 |
| WO | WO-9218627 A1 | 10/1992 |
| WO | WO-9400140 A1 | 1/1994 |
| WO | WO-9426298 A1 | 11/1994 |
| WO | WO-9532724 A1 | 12/1995 |
| WO | WO-9615812 A1 | 5/1996 |
| WO | WO-9709425 A1 | 3/1997 |
| WO | WO-9903973 A1 | 1/1999 |
| WO | WO-9918976 A1 | 4/1999 |

OTHER PUBLICATIONS

"Consensus Recommendations for the Management of Chronic Heart Failure." *Am. J. Cardiol*, 83.2A(1999):1A-38A.
Aikawa. "Formation Mechanism of Disease." *Igakunoyami (Progression of Medical Science)*. 185.1(1998):45-48.
Arbustini et al. "Coexistence of Mitochondrial DNA and β Myosin Heavy Chain Mutations in Hypertrophic Cardiomyopathy With Late Congestive heart Failure." *Heart.* 80.6(1998):548-558.
Bachinski et al. "New Theories: Causes of Dilated Cardiomyopathy." *Cardiol. Clin.* 16.4(1998):603-610.
Baglia et al. "NRG-1 Induced Cardiomyocyte Hypertrophy." *Am. J. Physiol.* 277(1999):H2026-H2037.
Balligand et al. "Cardiac Endothelium and Tissue Growth." *Prog. Cardiovasc. Dis.* 39(1997):351-360.

(Continued)

*Primary Examiner* — Sharon Wen
(74) *Attorney, Agent, or Firm* — Mintz Levin Cohn Ferris Glovsky and Popeo, P.C.; John A. Bauer; Katherine J. Miller

(57) ABSTRACT

The invention features methods of treating or preventing congestive heart failure by administering a polypeptide containing an epidermal growth factor-like domain encoded by a neuregulin gene.

26 Claims, 12 Drawing Sheets

OTHER PUBLICATIONS

Bargmann et al. "The Neu Oncogene Encodes an Epidermal Growth Factor Receptor-Related Protein." *Nature.* 319(1986):226-230.

Berger et al. "Continual Electric Field Stimulation Preserves Contractile Function of Adult Ventricular Myocytes in Primary Culture." *Am. J. Physiol.* 266(1994):H341-H349.

Berk et al. "Angiotensin II-Stimulated Protein Synthesis in Cultured Vascular Smooth Muscle Cells." *Hypertension*, 13(1989):305-314.

Burden et al. "Neuregulins and Their Receptors: A Versatile Signaling Module in Organogenesis and Oncogenesis," *Neuron.* 18(1997):847-855.

Busfield et al. "Characterization of a Neuregulin-Related Gene, *Don-1*, That is Highly Expressed in Related Regions of the Cerebellum and Hippocampus." *Mol. Cell. Biol.* 17(1997):4007-4014.

Carraway et al. "Neuregulin-2, a New Ligand of ErbB3/ErbB4-Receptor Tyrosine Kinases." *Nature.* 387(1997):512-516.

Chang et al. "Ligand for ErB-Family Receptors Encoded by a Neuregulin-Like Gene." *Nature.* 387(1997):509-512.

Chen et al. "Expression of Multiple Neuregulin Transcripts in Postnatal Rat Brains." *J. Comp. Neurol.* 349(1994):389-400.

Chien et al. "Regulation of Cardiac Gene Expression During Myocardial Growth and Hypertrophy: Molecular Studies of an Adaptive Physiologic Response." *FASEB. J.* 5(1991):30307-3046.

Chomczynski et al. "Single-Step Method of RNA Isolation by Acid Guanidinium Thiocyanate-Phenol-Chloroform Extraction." *Anal. Biochem.* 162.1(1987):156-159.

Cohn et al. "A Dose-Dependent Increase in Mortality With Vesnarinone Among Patients With Severe Heart Failure." *New Engl. J. Med.* 339.25(1998):1810-1816.

Colucci et al. "Pathophysiology of Heart Failure." *Heart Disease; A Textbook of Cardiovascular Medicine.* Brauwald, ed. Philadelphia: W.B. Saunders Co. 5th Ed. (1997):394-420.

Corfas et al. "Differential Expression of ARIA Isoforms in the Rat Brain." *Neuron.* 14(1995):103-115.

Dias et al. "The Molecular Basis of Skeletal Muscle Differentiation." *Sem. Diagnostic Pathol.* 11(1994):3-14.

Ellingsen et al. "Adult Rat Ventricular Myocytes Cultured in Defined Medium: Phenotype and Electromechanical Function," *Am. J. Physiol.* 265(1993):H747-H754.

Epstein et al. "Biological Activity of Liposome-Encapsulated Murine Interferon γ is Mediated by a Cell Membrane Receptor," *PNAS.* 82(1985):3688-3692.

Erikson et al. "ErbB3 is Required for Normal Cerebellar and Cardiac Development: A Comparison with ErbB2- and Heregulin-Deficient Mice." *Development.* 124(1997):4999-5011.

Falls et al. "ARIA, A Protein That Stimulates Acetylcholine Receptor Synthesis, is a Member of the Neu Ligand Family," *Cell.* 72(1993):801-815.

Feldman et al. "Selective Changes in Cardiac Gene Expression During Compensated Hypertrophy and the Transition to Cardiac Decompensation in Rats With Chronic Aortic Banding." *Circ. Res.* 73(1993):184-192.

Florini et al. "Stimulation of Myogenic Differentiation by a Neuregulin, Glial Growth Factor 2." *J. Biol. Chem.* 271(1996):12699-12702.

Franz et al. "Analysis of Tissue-Specific Gene Delivery by Recombinant Adenoviruses Containing Cardiac-Specific Promoters." *Cardiovasc. Res.* 35.3(1997):560-566.

Gassmann et al. "Aberrant Neural and Cardiac Development in Mice Lacking the ErbB4 Neuregulin Receptor." *Nature.* 378(1995):390-394.

GenBank Accession No. AB005060, Nov. 11, 1997.

Herman et al. "Preclinical Animal Models of Cardiac Protection From Anthracycline-Induced Cardiotoxicity." *Semin. Oncol.* 25.4(1998):15-21.

Herman et al. "Use of Cardiac Troponin T Levels as an Indicator of Doxorubicin-Induced Cardiotoxicity." *Cancer Res.* 58(1998):195-197.

Higashiyama et al. "A Novel Brain-Derived Member of the Epidermal Growth Factor Family That Interacts With ErbB3 and ErbB4," *J. Biochem. (Tokyo).* 122(1997):675-680.

Hijazi et al. "NRG-3 in Human Breast Cancers: Activation of Multiple erbB3 Family Proteins." *Int. J. Oncol.* 13(1998):1061-1067.

Holmes et al. "Identification of Heregulin, A Specific Activator of $p185^{erbB2}$," *Science.* 256(1992):1205-1210.

Hwang et al. "Hepatic Uptake and Degradation of Unilamellar Sphingomyelin/Cholesterol Liposomes: A Kinetic Study." *PNAS.* 77(1980):4030-4034.

Imondi. "Preclinical Models of Cardiac Protection and Testing for Effects of Dexrazoxane on Doxorubican Antitiumor Effects." *Semin. Oncol.* 25.4S10(1998):22-30.

Ito et al. "Endothelin and Angiotensin II Stimulation of $Na^+-H^+$ Exchange is Impaired in Cardiac Hypertrophy." *J. Clin. Invest.* 99.1(1997):125-135.

Kagaya et al. "Long-Term Angiotensin-Converting Enzyme Inhibition With Fosinopril Improves Depressed Responsiveness to $Ca^{2+}$ in Myocytes From Aortic-Banded Rats." *Circulation.* 94(1996):2915-2922.

Kramer et al. "Neuregulins with an Ig-Like Domain are Essential for Mouse Myocardial and Neuronal Development." *PNAS.* 93(1996):4833-4838.

Kraus et al. "Isolation and Characterization of ERBB3, A Third Member of the ERBB/Epidermal Growth Factor Receptor Failure: Evidence for Overexpression in a Subset of Human Mammary Tumors." *PNAS.* 86(1989):9193-9197.

Labhasetwar et al. "Arterial Uptake of Biodegradeable Nanoparticles: Effect of Surface Modifications." *J. Pharma. Sci.* 87.10(1998):1229-1234.

Langer et al. "Biocompatibility of Polymeric Delivery Systems for Macromolecules." *J. Biomed. Mat. Res.* 15(1981):267-277.

Lee et al. "Requirement for Neuregulin Receptor erB2 in Neural and Cardiac Development." *Nature*, 378(1995):394-398.

Lemke. "Neuregulins in Development." *Mol. Cell. Neurosci.* 7(1996):247-262.

Lin et al. "Atrial Natriuretic Peptide Gene Delivery Reduces Stroke-Induced Mortality Rate in Dahl Salt-Sensitive Rats." *Hypertension.* 33(1999):219-224.

Litwin et al. "Serial Echocardiographic-Doppler Assessment of Left Ventricular Geometry and Function in Rats With Pressure-Overload Hypertrophy: Chronic Angiotensin-Converting Enzyme Inhibition Attenuates the Transition to Heart Failure." *Circulation.* 91(1995):2642-2654.

Liu et al. "Domain-Specific Gene Disruption Reveals Critical Regulation of Neuregulin Signaling by its Cytoplasmic Tail." *PNAS.* 95(1998):13024-13024.

Losordo et al. "Gene Therapy for Myocardial Angiogenesis: Initial Clinical Results With Direct Myocardial Injection of $phVEGF_{165}$ as Sole Therapy for Myocardial Ischemia." *Circulation.* 98(1998):2800-2804.

Marchionni et al. "Glial Growth Factors are Alternatively Spliced erbB2 Ligands Expressed in the Nervous System." *Nature.* 362(1993):312-318.

*Merck Manual of Diagnosis and Therapy.* Neers et al., eds. Whitehouse Station, NJ: Merck Research Laboratories. 17th Ed.(1999):1682-1692.

Meyer et al. "Distinct Isoforms of Neuregulin are Expressed in Mesenchymal and Neuronal Cells During Mouse Development." *PNAS.* 91(1994):1064-1068.

Meyer et al. "Isoform-Specific Expression and Function of Neuregulin." *Development.* 124(1997):3575-3586.

Meyer et al. "Multiple Essential Functions of Neuregulin in Development." *Nature.* 378(1995):386-390.

Mosmann. "Rapid Colorimetric Assay For Cellular Growth and Survival: Application to Proliferation and Cytotoxicity Assays," *J. Immunol. Meth.* 65.1-2(1983):55-63.

Myers. "The Role of Iron in Doxorubicin-Induced Cardiomyopathy." *Semin. Oncol.* 25.410(1998):10-14.

Nishigaki et al. "Apoptosis as the Origin of Heart Failure." *Igakunoyami (Progression of Medical Science).* 187.10(1998):865-569.

Orr-Urtreger et al. "Neural Expression and Chromosomal Mapping of Neu Differentiation Factor to 8p12-p21," *PNAS.* 90(1993):1867-1871.

Parker et al. "p53-Independent Expression of $p21^{Cip1}$ in Muscle and Other Terminally Differentiating Cells." *Science.* 267(1995):1024-1027.

Peles et al. "Isolation of the NeuHER-2 Stimulatory Ligand: A 44 kd Glycoprotein That Induces Differentiation of Mammary Tumor Cells." *Cell.* 69(1992):205-216.

Peles et al. "Neu and its Ligands: From an Oncogene to Neural Factors." *Bioessays.* 15(1993):815-824.

*Physician's Desk Reference.* Montvale, NJ: Medical Economics Data Production Co. (1994):2314-2320.

Pinkas-Kramarski et al. "Brain Neurons and Glial Cells Express Neu Differential Factor/Heregulin: A Survival Factor for Astrocytes." *PNAS.* 91(1994):9387-9391.

Pinkas-Kramarski et al. "Differential Expression of NDF/Neuregulin Receptors ErbB-3 and Involvement in Inhibition of Neuronal Differentiation." *Oncogene.* 15.23(1997):2803-2815.

Pinkas-Kramarski et al. "ErbB Tyrosine Kinases and the Two Neuregulin Families Constitute a Ligand-Receptor Network." *Mol. Cell. Biol.* 18(1998):6090-6101.

Plowman et al, "Ligand-Specific Activation of HER4/p180$^{erbB4}$, A Fourth Member of the Epidermal Growth Factor Receptor Family." *PNAS.* 90(1993):1746-1750.

Prentice et al. "Regulated Expression of a Foreign Gene Targeted to the Ischaemic Myocardium." *Cardiovasc. Res.* 35.3(1997):567-574.

Rohrbach et al. "Neuregulin in Cardiac Hypertrophy in Rats With Aortic Stenosis." *Circulation.* 100(1999):407-412.

Rumyantsev. "Interrelations of the Proliferation and Differentiation Processes During Cardiac Myogenesis, and Regeneration." *Int. Rev. Cytol.* 51(1977):187-273.

Sarker et al. "Quantitative Analysis of Her-2/neu (ERBB2) Gene Expression Using Reverse Transcriptase Polymerase Chain Reaction." *Diag. Mol. Pathol.* 2(1993):210-218.

Schunkert et al. "Alteration of Growth Responses in Established Cardiac Pressure Overload Hypertrophy in Rats With Aortic Banding." *J. Clin. Invest.* 96.6(1995):2768-2774.

Schunkert et al. "Distribution and Functional Significance of Cardiac Angiotensin Converting Enzyme in Hypertrophied Rat Hearts." *Circulation.* 87(1993):1328-1339.

Seidman et al. "The Structure of Rat Preproatrial Natruiretic Factor as Defined by a Complementary DNA Clone." *Science.* 225(1984):324-326.

Shani et al. "Skeletal Muscle Actin mRNA." *Nucl. Acids Res.* 9.3(1981):579-589.

Sharov et al. "Evidence of Cardiocyte Apoptosis in Myocardium of Dogs With Chronic Heart Failure." *Am. J. Pathol.* 148.1(1996):141-149.

Sidman et al. "Controlled Release of Macromolecules and Pharmaceuticals from Synthetic Polypeptides Based on Glutamic Acid." *Biopolymers.* 22(1983):547-556.

Simpson et al. "Myocyte Hypertrophy in Neonatal Rat Heart Cultures and Its Regulation by Serum and by Catecholamines." *Circ. Res.* 51(1982):787-801.

Siu et al. "Familial Dilated Cardiomyopathy Locus Maps to Chromosome 2q31." *Circulation.* 99(1999):1022-1026.

SOLVD Investigators. "Effect of Enalapril on Mortality and the Development of Heart Failure in Asymptomatic Patients with Reduced Left Ventricular Ejection Fractions." *N. Engl. J. Med.* 327.10(1992):685-691.

Springhorn et al. "Transcriptional Regulation in Cardiac Muscle." *J. Biol. Chem.* 267.20(1992):14360-14365.

Tajima et al. "Treatment With Growth Hormone Enhances Contractile Reserve and Intracellular Calcium Transients in Myocytes From Rats With Postinfarction Heart Failure." *Circulation.* 99(1999):127-134.

Tso et al. "Isolation and Characterization of Rat and Human Glyceraldehyde-3-Phosphate Dehydrogenase cDNAs: Genomic Complexity and Molecular Evolution of the Gene." *Nucl. Acids Res.* 13.7(1985):2485-2502.

Weinberg et al. "Angiotensin $AT_1$ Receptor Inhibition: Effects on Hypertrophic Remodeling and ACE Expression in Rats With Pressure-Overload Hypertrophy Due to Ascending Aortic Stenosis." *Circulation.* 95(1997):1592-1600.

Weinberg et al. "Angiotensin-Converting Enzyme Inhibition Prolongs Survival and Modifies the Transition to Heart Failure in Rats With Pressure Overload Hypertrophy Due to Ascending Aortic Stenosis." *Circulation.* 90(1994):1410-1422.

Wen et al. "Neu Differentiation Factor: A Transmembrane Glycoprotein Containing an EGF Domain and an Immunoglobulin Homology Unit." *Cell.* 69(1992):559-572.

Yayama et al. "Kallikrein Gene Delivery Attenuates Hypertension and Cardiac Hypertrophy and Enhances Renal Function in Goldblatt Hypertensive Rats." *Hypertension.* 31(1998):1104-1110.

Zhang et al. "Neuregulin-3 (NRG3): A Novel Neural Tissue-Enriched Protein That Binds and Activates ErbB4." *PNAS.* 94(1997):9562-9567.

Zhao et al. "Neuregulins Promote Survival and Growth of Cardiac Myocytes." *J. Biol. Chem.* 273.17(1998):10261-10269.

Zhao et al. "Selective Disruption of Neuregulin-1 Function in Vertebrate Embryos Using Ribozyme-tRNA Transgenes." *Development.* 125(1998):1899-1907.

Zhou et al. "Retinoid-Dependent Pathways Suppress Myocardial Cell Hypertrophy." *PNAS.* 92(1995):7391-7395.

* cited by examiner

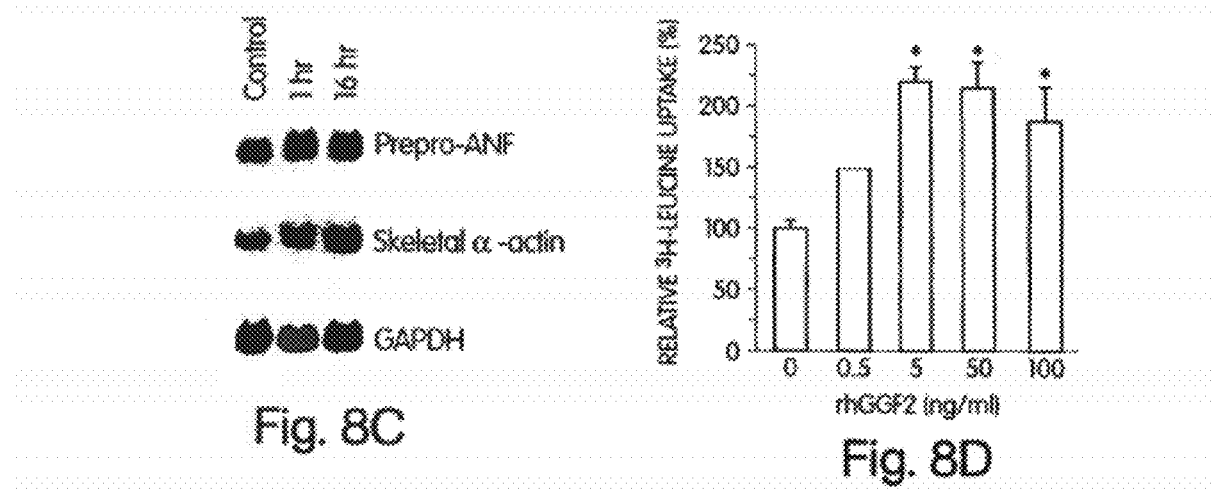

SEQUENCE LISTING

```
<160> NUMBER OF SEQ ID NOS: 14

<210> SEQ ID NO 1
<211> LENGTH: 25
<212> TYPE: DNA
<213> ORGANISM: Artificial Sequence
<220> FEATURE:
<223> OTHER INFORMATION: Synthetic primer

<400> SEQUENCE: 1
tgtgctagtc aagagtccca accac                                          25

<210> SEQ ID NO 2
<211> LENGTH: 25
<212> TYPE: DNA
<213> ORGANISM: Artificial Sequence
<220> FEATURE:
<223> OTHER INFORMATION: Synthetic primer

<400> SEQUENCE: 2
ccttctctcg gtactaagta ttcag                                          25

<210> SEQ ID NO 3
<211> LENGTH: 25
<212> TYPE: DNA
<213> ORGANISM: Artificial Sequence
<220> FEATURE:
<223> OTHER INFORMATION: Synthetic primer

<400> SEQUENCE: 3
gcttaaagtg cttggctcgg gtgtc                                          25

<210> SEQ ID NO 4
<211> LENGTH: 24
<212> TYPE: DNA
<213> ORGANISM: Artificial Sequence
<220> FEATURE:
<223> OTHER INFORMATION: Synthetic primer

<400> SEQUENCE: 4
tcctacacac tgacactttc tctt                                           24

<210> SEQ ID NO 5
<211> LENGTH: 26
<212> TYPE: DNA
<213> ORGANISM: Artificial Sequence
<220> FEATURE:
```

<223> OTHER INFORMATION: Synthetic primer

<400> SEQUENCE: 5
aattcaccca tcagagtgac gtttgg                                           26

<210> SEQ ID NO 6
<211> LENGTH: 23
<212> TYPE: DNA
<213> ORGANISM: Artificial Sequence
<220> FEATURE:
<223> OTHER INFORMATION: Synthetic primer

<400> SEQUENCE: 6
tcctgcaggt agtctgggtg ctg                                              23

<210> SEQ ID NO 7
<211> LENGTH: 24
<212> TYPE: DNA
<213> ORGANISM: Artificial Sequence
<220> FEATURE:
<223> OTHER INFORMATION: Synthetic primer

<400> SEQUENCE: 7
gctggctccg atgtatttga tggt                                             24

<210> SEQ ID NO 8
<211> LENGTH: 24
<212> TYPE: DNA
<213> ORGANISM: Artificial Sequence
<220> FEATURE:
<223> OTHER INFORMATION: Synthetic primer

<400> SEQUENCE: 8
gttctctgcc gtaggtgtcc cttt                                             24

<210> SEQ ID NO 9
<211> LENGTH: 22
<212> TYPE: DNA
<213> ORGANISM: Artificial Sequence
<220> FEATURE:
<223> OTHER INFORMATION: Synthetic primer

<400> SEQUENCE: 9
gcatcactgg ctgattctgg ag                                               22

<210> SEQ ID NO 10
<211> LENGTH: 22
<212> TYPE: DNA
<213> ORGANISM: Artificial Sequence
<220> FEATURE:
<223> OTHER INFORMATION: Synthetic primer

<400> SEQUENCE: 10
cacatgccgg ttatggtcag ca                                               22

<210> SEQ ID NO 11
<211> LENGTH: 754
<212> TYPE: PRT
<213> ORGANISM: Rattus norvegicus

<400> SEQUENCE: 11

Met Arg Arg Asp Pro Ala Pro Gly Phe Ser Met Leu Leu Phe Gly Val
1               5                   10                  15

Ser Leu Ala Cys Tyr Ser Pro Ser Leu Lys Ser Val Gln Asp Gln Ala
            20                  25                  30

-continued

```
Tyr Lys Ala Pro Val Val Glu Gly Lys Val Gln Gly Leu Ala Pro
         35                  40                  45
Ala Gly Gly Ser Ser Asn Ser Thr Arg Glu Pro Pro Ala Ser Gly
 50                  55                  60
Arg Val Ala Leu Val Lys Val Leu Asp Lys Trp Pro Leu Arg Ser Gly
 65                  70                  75                  80
Gly Leu Gln Arg Glu Gln Val Ile Ser Val Gly Ser Cys Ala Pro Leu
             85                  90                  95
Glu Arg Asn Gln Arg Tyr Ile Phe Phe Leu Glu Pro Thr Glu Gln Pro
                100                 105                 110
Leu Val Phe Lys Thr Ala Phe Ala Pro Val Asp Pro Asn Gly Lys Asn
        115                 120                 125
Ile Lys Lys Glu Val Gly Lys Ile Leu Cys Thr Asp Cys Ala Thr Arg
    130                 135                 140
Pro Lys Leu Lys Lys Met Lys Ser Gln Thr Gly Glu Val Gly Glu Lys
145                 150                 155                 160
Gln Ser Leu Lys Cys Glu Ala Ala Gly Asn Pro Gln Pro Ser Tyr
                165                 170                 175
Arg Trp Phe Lys Asp Gly Lys Glu Leu Asn Arg Ser Arg Asp Ile Arg
                180                 185                 190
Ile Lys Tyr Gly Asn Gly Arg Lys Asn Ser Arg Leu Gln Phe Asn Lys
        195                 200                 205
Val Lys Val Glu Asp Ala Gly Glu Tyr Val Cys Glu Ala Glu Asn Ile
    210                 215                 220
Leu Gly Lys Asp Thr Val Arg Gly Arg Leu His Val Asn Ser Val Ser
225                 230                 235                 240
Thr Thr Leu Ser Ser Trp Ser Gly His Ala Arg Lys Cys Asn Glu Thr
                245                 250                 255
Ala Lys Ser Tyr Cys Val Asn Gly Gly Val Cys Tyr Tyr Ile Glu Gly
                260                 265                 270
Ile Asn Gln Leu Ser Cys Lys Cys Pro Val Gly Tyr Thr Gly Asp Arg
        275                 280                 285
Cys Gln Gln Phe Ala Met Val Asn Phe Ser Lys His Leu Gly Phe Glu
    290                 295                 300
Leu Lys Glu Ala Glu Glu Leu Tyr Gln Lys Arg Val Leu Thr Ile Thr
305                 310                 315                 320
Gly Ile Cys Val Ala Leu Leu Val Val Gly Ile Val Cys Val Val Ala
                325                 330                 335
Tyr Cys Lys Thr Lys Lys Gln Arg Arg Gln Met His His Leu Arg
                340                 345                 350
Gln Asn Met Cys Pro Ala His Gln Asn Arg Ser Leu Ala Asn Gly Pro
        355                 360                 365
Ser His Pro Arg Leu Asp Pro Glu Glu Ile Gln Met Ala Asp Tyr Ile
    370                 375                 380
Ser Lys Asn Val Pro Ala Thr Asp His Val Ile Arg Arg Glu Ala Glu
385                 390                 395                 400
Thr Thr Phe Ser Gly Ser His Ser Cys Ser Pro Ser His His Cys Ser
                405                 410                 415
Thr Ala Thr Pro Thr Ser Ser His Arg His Glu Ser His Thr Trp Ser
                420                 425                 430
Leu Glu Arg Ser Glu Ser Leu Thr Ser Asp Ser Gln Ser Gly Ile Met
        435                 440                 445
Leu Ser Ser Val Gly Thr Ser Lys Cys Asn Ser Pro Ala Cys Val Glu
    450                 455                 460
```

Ala Arg Ala Arg Arg Ala Ala Tyr Ser Gln Glu Arg Arg
465                 470                 475                 480

Ala Ala Met Pro Pro Tyr His Asp Ser Ile Asp Ser Leu Arg Asp Ser
                485                 490                 495

Pro His Ser Glu Arg Tyr Val Ser Ala Leu Thr Thr Pro Ala Arg Leu
            500                 505                 510

Ser Pro Val Asp Phe His Tyr Ser Leu Ala Thr Gln Val Pro Thr Phe
            515                 520                 525

Glu Ile Thr Ser Pro Asn Ser Ala His Ala Val Ser Leu Pro Pro Ala
        530                 535                 540

Ala Pro Ile Ser Tyr Arg Leu Ala Glu Gln Gln Pro Leu Leu Gly His
545                 550                 555                 560

Pro Ala Pro Pro Gly Pro Gly Pro Gly Ala Asp Met Gln Arg
                565                 570                 575

Ser Tyr Asp Ser Tyr Tyr Tyr Pro Ala Ala Gly Pro Gly Pro Arg Arg
            580                 585                 590

Gly Ala Cys Ala Leu Gly Gly Ser Leu Gly Ser Leu Pro Ala Ser Pro
            595                 600                 605

Phe His Ile Pro Glu Asp Asp Glu Tyr Glu Thr Thr Gln Glu Cys Ala
            610                 615                 620

Pro Pro Pro Pro Pro Arg Pro Arg Thr Arg Gly Ala Ser Arg Arg Thr
625                 630                 635                 640

Ser Ala Gly Pro Arg Arg Trp Arg Arg Ser Arg Leu Asn Gly Leu Ala
                645                 650                 655

Ala Gln Arg Ala Arg Ala Arg Asp Ser Leu Ser Leu Ser Ser Gly
            660                 665                 670

Ser Gly Cys Gly Ser Ala Ser Ala Ser Asp Asp Ala Asp Ala
            675                 680                 685

Asp Gly Ala Leu Ala Ala Glu Ser Thr Pro Phe Leu Gly Leu Arg Ala
            690                 695                 700

Ala His Asp Ala Leu Arg Ser Asp Ser Pro Pro Leu Cys Pro Ala Ala
705                 710                 715                 720

Asp Ser Arg Thr Tyr Tyr Ser Leu Asp Ser His Ser Thr Arg Ala Ser
                725                 730                 735

Ser Arg His Ser Arg Gly Pro Pro Thr Arg Ala Lys Gln Asp Ser Gly
            740                 745                 750

Pro Leu

<210> SEQ ID NO 12
<211> LENGTH: 330
<212> TYPE: PRT
<213> ORGANISM: Rattus norvegicus

<400> SEQUENCE: 12

Met Arg Arg Asp Pro Ala Pro Gly Phe Ser Met Leu Leu Phe Gly Val
1               5                   10                  15

Ser Leu Ala Cys Tyr Ser Pro Ser Leu Lys Ser Val Gln Asp Gln Ala
                20                  25                  30

Tyr Lys Ala Pro Val Val Val Glu Gly Lys Val Gln Gly Leu Ala Pro
            35                  40                  45

Ala Gly Gly Ser Ser Ser Asn Ser Thr Arg Glu Pro Pro Ala Ser Gly
        50                  55                  60

Arg Val Ala Leu Val Lys Val Leu Asp Lys Trp Pro Leu Arg Ser Gly
65                  70                  75                  80

```
Gly Leu Gln Arg Glu Gln Val Ile Ser Val Gly Ser Cys Ala Pro Leu
                85                  90                  95

Glu Arg Asn Gln Arg Tyr Ile Phe Phe Leu Glu Pro Thr Gln Gln Pro
            100                 105                 110

Leu Val Phe Lys Thr Ala Phe Ala Pro Val Asp Pro Asn Gly Lys Asn
        115                 120                 125

Ile Lys Lys Glu Val Gly Lys Ile Leu Cys Thr Asp Cys Ala Thr Arg
    130                 135                 140

Pro Lys Leu Lys Lys Met Lys Ser Gln Thr Gly Glu Val Gly Glu Lys
145                 150                 155                 160

Gln Ser Leu Lys Cys Glu Ala Ala Gly Asn Pro Gln Pro Ser Tyr
                165                 170                 175

Arg Trp Phe Lys Asp Gly Lys Glu Leu Asn Arg Ser Arg Asp Ile Arg
            180                 185                 190

Ile Lys Tyr Gly Asn Gly Arg Lys Asn Ser Arg Leu Gln Phe Asn Lys
        195                 200                 205

Val Lys Val Glu Asp Ala Gly Glu Tyr Val Cys Glu Ala Glu Asn Ile
    210                 215                 220

Leu Gly Lys Asp Thr Val Arg Gly Arg Leu His Val Asn Ser Val Ser
225                 230                 235                 240

Thr Thr Leu Ser Ser Trp Ser Gly His Ala Arg Lys Cys Asn Glu Thr
                245                 250                 255

Ala Lys Ser Tyr Cys Val Asn Gly Gly Val Cys Tyr Tyr Ile Glu Gly
            260                 265                 270

Ile Asn Gln Leu Ser Cys Lys Cys Pro Asn Gly Phe Phe Gly Gln Arg
        275                 280                 285

Cys Leu Glu Lys Leu Pro Leu Arg Leu Tyr Met Pro Asp Pro Lys Gln
    290                 295                 300

Ser Val Leu Trp Asp Thr Pro Gly Thr Gly Val Ser Ser Gln Trp
305                 310                 315                 320

Ser Thr Ser Pro Ser Thr Leu Asp Leu Asn
                325                 330

<210> SEQ ID NO 13
<211> LENGTH: 182
<212> TYPE: PRT
<213> ORGANISM: Homo sapiens

<400> SEQUENCE: 13

Arg Gly Glu Gly Ile Ser Phe Pro Ser Lys Leu Gln Gly His Cys Gly
1               5                   10                  15

Ser Val Glu Arg Gly Asn Arg Trp Val Thr Ala Gly Glu Pro Gln Pro
            20                  25                  30

Ala Leu Ala His Ala Ser Pro Pro Phe Ile Pro Ser Leu Thr Arg Lys
        35                  40                  45

Asn Ser Arg Leu Gln Phe Asn Lys Val Lys Val Glu Asp Ala Gly Glu
    50                  55                  60

Tyr Val Cys Glu Ala Glu Asn Ile Leu Gly Lys Asp Thr Val Arg Gly
65                  70                  75                  80

Arg Leu Tyr Val Asn Ser Val Ser Thr Thr Leu Ser Ser Trp Ser Gly
                85                  90                  95

His Ala Arg Lys Cys Asn Glu Thr Ala Lys Ser Tyr Cys Val Asn Gly
            100                 105                 110

Gly Val Cys Tyr Tyr Ile Glu Gly Ile Asn Gln Leu Ser Cys Lys Cys
        115                 120                 125
```

```
Pro Asn Gly Phe Phe Gly Gln Arg Cys Leu Glu Lys Leu Pro Leu Arg
    130                 135                 140

Leu Tyr Met Pro Asp Pro Lys Gln Ser Val Leu Trp Asp Thr Pro Gly
145                 150                 155                 160

Thr Gly Val Ser Ser Gln Trp Ser Thr Pro Lys Pro Arg Ser
                165                 170                 175

Cys Thr Arg Arg Gly Ser
        180

<210> SEQ ID NO 14
<211> LENGTH: 3020
<212> TYPE: DNA
<213> ORGANISM: Homo sapiens

<400> SEQUENCE: 14
```

| | | | | | |
|---|---|---|---|---|---|
| cctccaggtc | ctggcgcaca | gggtgggagc | gctgcgctgc | gccgcgctgc | gcatcgcggc | 60 |
| ccgcttgccg | cctgccccct | gccctagctg | ggccacctcc | ccgggctgcc | ggtggagggc | 120 |
| taagaggcgc | taacgttacg | ctgtttccgg | ttttccagcg | ggctctgttt | cccctcccaa | 180 |
| ggcggcggcg | gctgagcggc | ggagcccccc | aaatggcctg | ccagatgcg | gcaggtttgc | 240 |
| tgctcagcgc | tgccgccgcc | gccactggag | aagggtcggt | gcagcagcta | cagcgacagc | 300 |
| agcagcagca | gcagcgagag | gagcagcagc | agcagcagca | gcagcagcga | gagcggcagc | 360 |
| agcagcagga | gcagcagcaa | caacagcagc | atctctcgtc | ccgctgcgcc | cccagagccg | 420 |
| cggccgcagc | aacagccgca | gccccgcagc | cccgcagccc | ggagagccgc | cgcccgttcg | 480 |
| cgagccgcag | ccgccggcgg | catgaggcgc | gacccggccc | ccggcttctc | catgctgctc | 540 |
| ttcggtgtgt | cgctcgcctg | ctactcgccc | agcctcaagt | cagtgcagga | ccaggcgtac | 600 |
| aaggcacccg | tggtggtgga | gggcaaggta | caggggctgg | tccagccgg | cggctccagc | 660 |
| tccaacagca | cccgagagcc | gccgccctcg | ggtcggtgg | cgttggtaaa | ggtgctggac | 720 |
| aagtggccgc | tccggagcgg | ggggctgcag | cgcgagcagg | tgatcagcgt | gggctcctgt | 780 |
| gtgccgctcg | aaaggaacca | gcgctacatc | ttttttcctgg | agcccacgga | acagcccttα | 840 |
| gtctttaaga | cggcctttgc | cccccctcgat | accaacggca | aaaatctcaa | gaaagaggtg | 900 |
| ggcaagatcc | tgtgcactga | ctgcgccacc | cggcccaagt | tgaagaagat | gaagagccag | 960 |
| acgggacagg | tgggtgagaa | gcaatcgctg | aagtgtgagg | cagcagccgg | taatccccag | 1020 |
| ccttcctacc | gttggttcaa | ggatggcaag | gagctcaacc | gcagccgaga | cattcgcatc | 1080 |
| aaatatggca | acggcagaaa | gaactcacga | ctacagttca | acaaggtgaa | ggtggaggac | 1140 |
| gctggggagt | atgtctgcga | ggccgagaac | atcctgggga | aggacaccgt | ccggggccgg | 1200 |
| ctttacgtca | cagcgtgag | caccaccctg | tcatcctggt | cggggcacgc | ccggaagtgc | 1260 |
| aacgagacag | ccaagtccta | ttgcgtcaat | ggaggcgtct | gctactacat | cgagggcatc | 1320 |
| aaccagctct | cctgcaaatg | tccaaatgga | ttcttcggac | agagatgttt | ggagaaactg | 1380 |
| cctttgcgat | tgtacatgcc | agatcctaag | caaaaagccg | aggagctgta | ccagaagagg | 1440 |
| gtcctgacca | tcacgggcat | ctgcgtggct | ctgctggtcg | tgggcatcgt | ctgtgtggtg | 1500 |
| gcctactgca | agaccaaaaa | acagcggaag | cagatgcaca | accacctccg | gcagaacatg | 1560 |
| tgcccggccc | atcagaaccg | gagcttggcc | aatgggccca | gcaccccccg | gctgacccca | 1620 |
| gaggagatcc | agatggcaga | ttatatttcc | aagaacgtgc | cagccacaga | ccatgtcatc | 1680 |
| aggagagaaa | ctgagaccac | cttctctggg | agccactcct | gttctccttc | tcaccactgc | 1740 |
| tccacagcca | cacccaacctc | cagccacaga | cacgagagcc | acacgtggag | cctggaacgt | 1800 |

```
tctgagagcc tgacttctga ctcccagtcg gggatcatgc tatcatcagt gggtaccagc    1860
aaatgcaaca gcccagcatg tgtggaggcc cgggcaaggc gggcagcagc ctacaacctg    1920
gaggagcggc gcagggccac cgcgccaccc tatcacgatt ccgtggactc ccttcgcgac    1980
tccccacaca gcgagaggta cgtgtcggcc ctgaccacgc ccgcgcgcct ctcgcccgtg    2040
gacttccact actcgctggc cacgcaggtg ccaactttcg agatcacgtc ccccaactcg    2100
gcgcacgccg tgtcgctgcc gccggcggcg cccatcagtt accgcctggc cgagcagcag    2160
ccgttactgc ggcacccggc gccccccggc ccgggacccg gacccgggcc cgggcccggg    2220
cccggcgcag acatgcagcg cagctatgac agctactatt accccgcggc ggggcccgga    2280
ccgcggcgcg ggacctgcgc gctcggcggc agcctgggca gcctgcctgc cagcccctc    2340 cgcatccccg aggacgacga gtacgagacc acgcaggagt gcgcgccccc gccgccgccg    2400
cggccgcgcg cgcgcggtgc gtcccgcagg acgtcggcgg ggccccggcg ctggcgccgc    2460
tcgcgcctca acgggctggc ggcgcagcgc gcacgggcgg cgagggactc gctgtcgctg    2520
agcagcggct cgggcggcgg ctcagcctcg gcgtcggacg acgacgcgga cgacgcggac    2580
ggggcgctgg cggccgagag cacacctttc ctgggcctgc gtggggcgca cgacgcgctg    2640
cgctcggact tgccgccact gtgcccggcg gccgacagca ggacttacta ctcactggac    2700
agccacagca cgcgggccag cagcagacac agccgcgggc cgccccgcg ggccaagcag    2760 gactcggcgc cactctaggg ccccgccgcg cgcccctccg ccccgcccgc cccactatct    2820
ttaaggagac cagagaccgc ctactggaga gaaaggagga aaaaagaaat aaaaatattt    2880
ttattttcta taaaaggaaa aaagtataac aaaatgtttt attttcattt tagcaaaaat    2940
tgtcttataa tactagctaa cggcaaaggc gttttttatag ggaaactatt tatatgtaac    3000
atcctgattt acagcttcgg                                                3020
```

METHODS FOR TREATING CONGESTIVE HEART FAILURE

This application is a continuation of application Ser. No. 12/655,361 filed Dec. 29, 2009, now U.S. Pat. No. 8,076,283, which is a divisional of application Ser. No. 10/646,268 filed Aug. 22, 2003, now U.S. Pat. No. 7,662,772, which is a divisional of application Ser. No. 09/298,121 filed Apr. 23, 1999, now U.S. Pat. No. 6,635,249, the contents of which are each hereby incorporated by reference in their entireties.

STATEMENT AS TO FEDERALLY SPONSORED RESEARCH

This work was supported in part by NIH Grants HL-38189, HL-36141, and a NASA award. The government has certain rights in the invention.

FIELD OF THE INVENTION

The field of the invention is treatment and prevention of congestive heart failure.

BACKGROUND OF THE INVENTION

Congestive heart failure, one of the leading causes of death in industrialized nations, results from an increased workload on the heart and a progressive decrease in its pumping ability. Initially, the increased workload that results from high blood pressure or loss of contractile tissue induces compensatory cardiomyocyte hypertrophy and thickening of the left ventricular wall, thereby enhancing contractility and maintaining cardiac function. However, over time, the left ventricular chamber dilates, systolic pump function deteriorates, cardiomyocytes undergo apoptotic cell death, and myocardial function progressively deteriorates.

Factors that underlie congestive heart failure include high blood pressure, ischemic heart disease, exposure to cardiotoxic compounds such as the anthracycline antibiotics, and genetic defects known to increase the risk of heart failure.

Neuregulins (NRGs) and NRG receptors comprise a growth factor-receptor tyrosine kinase system for cell-cell signalling that is involved in organogenesis in nerve, muscle, epithelia, and other tissues (Lemke, *Mol. Cell. Neurosci.* 7: 247-262, 1996 and Burden et al., *Neuron* 18: 847-855, 1997). The NRG family consists of three genes that encode numerous ligands containing epidermal growth factor (EGF)-like, immunoglobulin (Ig), and other recognizable domains. At least 20 (perhaps 50 or more) secreted and membrane-attached isoforms may function as ligands in this signalling system. The receptors for NRG ligands are all members of the EGF receptor (EGFR) family, and include EGFR (or ErbB1), ErbB2, ErbB3, and ErbB4, also known as HER1 through HER4, respectively, in humans (Meyer et al., *Development* 124: 3575-3586, 1997; Orr-Urtreger et al., *Proc. Natl. Acad. Sci. USA* 90: 1867-71, 1993; Marchionni et al., *Nature* 362: 312-8, 1993; Chen et al., *J. Comp. Neurol.* 349: 389-400, 1994; Corfas et al., *Neuron* 14: 103-115, 1995; Meyer et al., *Proc. Natl. Acad. Sci. USA* 91:1064-1068, 1994; and Pinkas-Kramarski et al., *Oncogene* 15: 2803-2815, 1997).

The three NRG genes, Nrg-1, Nrg-2, and Nrg-3, map to distinct chromosomal loci (Pinkas-Kramarski et al., *Proc. Natl. Acad. Sci. USA* 91: 9387-91, 1994; Carraway et al., *Nature* 387: 512-516, 1997; Chang et al., *Nature* 387: 509-511, 1997; and Zhang et al., *Proc. Natl. Acad. Sci. USA* 94: 9562-9567, 1997), and collectively encode a diverse array of NRG proteins. The most thoroughly studied to date are the gene products of Nrg-1, which comprise a group of approximately 15 distinct structurally-related isoforms (Lemke, *Mol. Cell. Neurosci.* 7: 247-262, 1996 and Peles and Yarden, *BioEssays* 15: 815-824, 1993). The first-identified isoforms of NRG-1 included Neu Differentiation Factor (NDF; Peles et al., *Cell* 69, 205-216, 1992 and Wen et al., *Cell* 69, 559-572, 1992), Heregulin (HRG; Holmes et al., *Science* 256: 1205-1210, 1992), Acetylcholine Receptor Inducing Activity (ARIA; Falls et al., *Cell* 72: 801-815, 1993), and the glial growth factors GGF1, GGF2, and GGF3 (Marchionni et al. *Nature* 362: 312-8, 1993).

The Nrg-2 gene was identified by homology cloning (Chang et al., *Nature* 387:509-512, 1997; Carraway et al., *Nature* 387:512-516, 1997; and Higashiyama et al., *J. Biochem,* 122: 675-680, 1997) and through genomic approaches (Busfield et al., *Mol. Cell. Biol.* 17:4007-4014, 1997). NRG-2 cDNAs are also known as Neural- and Thymus-Derived Activator of ErbB Kinases (NTAK; Genbank Accession No. AB005060), Divergent of Neuregulin (Don-1), and Cerebellum-Derived Growth Factor (CDGF; PCT application WO 97/09425). Experimental evidence shows that cells expressing ErbB4 or the ErbB2/ErbB4 combination are likely to show a particularly robust response to NRG-2 (Pinkas-Kramarski et al., *Mol. Cell. Biol.* 18: 6090-6101, 1998). The Nrg-3 gene product (Zhang et al., supra) is also known to bind and activate ErbB4 receptors (Hijazi et al., *Int. J. Oncol.* 13:1061-1067, 1998).

An EGF-like domain is present at the core of all forms of NRGs, and is required for binding and activating ErbB receptors. Deduced amino acid sequences of the EGF-like domains encoded in the three genes are approximately 30-40% identical (pairwise comparisons). Further, there appear to be at least two sub-forms of EGF-like domains in NRG-1 and NRG-2, which may confer different bioactivities and tissue-specific potencies.

Cellular responses to NRGs are mediated through the NRG receptor tyrosine kinases EGFR, ErbB2, ErbB3, and ErbB4 of the epideimal growth factor receptor family. High-affinity binding of all NRGs is mediated principally via either ErbB3 or ErbB4. Binding of NRG ligands leads to dimerization with other ErbB subunits and transactivation by phosphorylation on specific tyrosine residues. In certain experimental settings, nearly all combinations of ErbB receptors appear to be capable of forming dimers in response to the binding of NRG-1 isoforms, However, it appears that ErbB2 is a preferred dimerization partner that may play an important role in stabilizing the ligand-receptor complex. Recent evidence has shown that expression of NRG-1, ErbB2, and ErbB4 is necessary for trabeculation of the ventricular myocardium during mouse development.

In view of the high prevalence of congestive heart failure in the general population, it would be highly beneficial to prevent or minimize progression of this disease by inhibiting loss of cardiac function, and ideally, by improving cardiac function for those who have or are at risk for congestive heart failure.

SUMMARY OF THE INVENTION

We have found that neuregulins stimulate compensatory hypertrophic growth and inhibit apoptosis of myocardiocytes subjected to physiological stress. Our observations indicate that neuregulin treatment will be useful for preventing, minimizing, or reversing congestive heart disease resulting from underlying factors such as hypertension, ischemic heart disease, and cardiotoxicity.

The invention provides a method for treating or preventing congestive heart failure in a mammal. The method involves administering a polypeptide that contains an epidermal growth factor-like (EGF-like) domain to the mammal, wherein the EGF-like domain is encoded by a neuregulin gene, and wherein administration of the polypeptide is in an amount effective to treat or prevent heart failure in the mammal.

In various preferred embodiments of the invention, the neuregulin gene may be the NRG-1 gene, the NRG-2 gene, or the NRG-3 gene. Furthermore, the polypeptide may be encoded by any of these three neuregulin genes. Still further, the polypeptide used in the method may be recombinant human GGF2.

In another preferred embodiment of the invention, the mammal is a human.

In other embodiments of the invention, the congestive heart failure may result from hypertension, ischemic heart disease, exposure to a cardiotoxic compound (e.g., cocaine, alcohol, an anti-ErbB2 antibody or anti-HER2 antibody, such as HERCEPTIN®, or an anthracycline antibiotic, such as doxorubicin or daunomycin), myocarditis, thyroid disease, viral infection, gingivitis, drug abuse; alcohol abuse, periocarditis, atherosclerosis, vascular disease, hypertrophic cardiomyopathy, acute myocardial infarction or previous myocardial infarction, left ventricular systolic dysfunction, coronary bypass surgery, starvation, an eating disorder, or a genetic defect.

In another embodiment of the invention, an anti-ErB2 or anti4HER2 antibody, such as HERCEPTIN®, is administered to the mammal either before, during, or after anthracycline administration.

In other embodiments of the invention, the polypeptide containing an EGF-like domain encoded by a neuregulin gene is administered before, during, or after exposure to a cardiotoxic compound. In yet other embodiments, the polypeptide containing the EGF-like domain is administered during two, or all three, of these periods.

In still other embodiments of the invention, the polypeptide is administered either prior to or after the diagnosis of congestive heart failure in the mammal.

In yet another embodiment of the invention, the polypeptide is administered to a mammal that has undergone compensatory cardiac hypertrophy.

In other preferred embodiments of the invention, administration of the polypeptide maintains left ventricular hypertrophy, prevents progression of myocardial thinning, or inhibits cardiomyocyte apoptosis.

In yet another embodiment of the invention, the polypeptide may be administered by administering an expression vector encoding the polypeptide to the mammal.

By "congestive heart failure" is meant impaired cardiac function that renders the heart unable to maintain the normal blood output at rest or with exercise, or to maintain a normal cardiac output in the setting of normal cardiac filling pressure. A left ventricular ejection fraction of about 40% or less is indicative of congestive heart failure (by way of comparison, an ejection fraction of about 60% percent is normal). Patients in congestive heart failure display well-known clinical symptoms and signs, such as tachypnea, pleural effusions, fatigue at rest or with exercise, contractile dysfunction, and edema. Congestive heart failure is readily diagnosed by well known methods (see, e.g., "Consensus recommendations for the management of chronic heart failure." *Am. J. Cardiol.,* 83(2A):1A-38-A, 1999).

Relative severity and disease progression are assessed using well known methods, such as physical examination, echocardiography, radionuclide imaging, invasive hemodynamic monitoring, magnetic resonance angiography, and exercise treadmill testing coupled with oxygen uptake studies.

By "ischemic heart disease" is meant any disorder resulting from an imbalance between the myocardial need for oxygen and the adequacy of the oxygen supply. Most cases of ischemic heart disease result from narrowing of the coronary arteries, as occurs in atherosclerosis or other vascular disorders.

By "myocardial infarction" is meant a process by which ischemic disease results in a region of the myocardium being replaced by scar tissue.

By "cardiotoxic" is meant a compound that decreases heart function by directing or indirectly impairing or killing cardiomyocytes.

By "hypertension" is meant blood pressure that is considered by a medical professional (e.g., a physician or a nurse) to be higher than normal and to carry an increased risk for developing congestive heart failure.

By "treating" is meant that administration of a neuregulin or neuregulin-like polypeptide slows or inhibits the progression of congestive heart failure during the treatment, relative to the disease progression that would occur in the absence of treatment, in a statistically significant manner. Well known indicia such as left ventricular ejection fraction, exercise performance, and other clinical tests as enumerated above, as well as survival rates and hospitalization rates may be used to assess disease progression. Whether or not a treatment slows or inhibits disease progression in a statistically significant manner may be determined by methods that are well known in the art (see, e.g., SOLVD Investigators, *N. Engl. J. Med.* 327:685-691, 1992 and Cohn et al., *N. Engl. J. Med.* 339: 1810-4816, 1998).

By "preventing" is meant minimizing or partially or completely inhibiting the development of congestive heart failure in a mammal at risk for developing congestive heart failure (as defined in "Consensus recommendations for the management of chronic heart failure." *Am. J. Cardiol.,* 83(2A): 1A38-A, 1999). Determination of whether congestive heart failure is minimized or prevented by administration of a neurgulin or neuregulin-like polypeptide is made by known methods, such as those described in SOLVD Investigators, supra, and Cohn et al., supra.

By "at risk for congestive heart failure" is meant an individual who smokes, is obese (i.e., 20% or more over their ideal weight), has been or will be exposed to a cardiotoxic compound (such as an anthracycline antibiotic), or has (or had) high blood pressure, ischemic heart disease, a myocardial infarct, a genetic defect known to increase the risk of heart failure, a family history of heart failure, myocardial hypertrophy, hypertrophic cardiomyopathy, left ventricular systolic dysfunction, coronary bypass surgery, vascular disease, atherosclerosis, alcoholism, periocarditis, a viral infection, gingivitis, or an eating disorder (e.g., anorexia nervosa or bulimia), or is an alcoholic or cocaine addict.

By "decreasing progression of myocardial thinning" is meant maintaining hypertrophy of ventricular cardiomyocytes such that the thickness of the ventricular wall is maintained or increased.

By "inhibits myocardial apoptosis" is meant that neuregulin treatment inhibits death of cardiomyocytes by at least 10%, more preferably by at least 15%, still more preferably by at least 25%, even more preferably by at least 50%, yet more preferably by at least 75%, and most preferably by at least 90%, compared to untreated cardiomyocytes.

By "neuregulin" or "NRG" is meant a polypeptide that is encoded by an NRG-1, NRG-2, or NRG-3 gene or nucleic acid (e.g., a cDNA), and binds to and activates ErbB2, ErbB3, or ErbB4 receptors, or combinations thereof.

By "neuregulin-1," "NRG-1," "heregulin," "GGF2," or "p185erbB2 ligand" is meant a polypeptide that binds to the ErbB2 receptor and is encoded by the p185erbB2 ligand gene described in U.S. Pat. No. 5,530,109; U.S. Pat. No. 5,716, 930; and U.S. Ser. No. 08/461,097.

By "neuregulin-like polypeptide" is meant a polypeptide that possesses an EGF-like domain encoded by a neuregulin gene, and binds to and activates ErbB-2, ErbB-3, ErbB-4, or a combination thereof.

By "epidermal growth factor-like domain" or "EGF-like domain" is meant a polypeptide motif encoded by the NRG-1, NRG-2, or NRG-3 gene that binds to and activates ErbB2, ErbB3, ErbB4, or combinations thereof, and bears a structural similarity to the EGF receptor-binding domain as disclosed in Holmes et al., Science 256:1205-1210, 1992; U.S. Pat. No. 5,530,109; U.S. Pat. No. 5,716,930; U.S. Ser. No. 08/461, 097; Hijazi et al., Int. J. Oncol. 13:1061-1067, 1998; Chang et al., Nature 387:509-512, 1997; Carraway et al., Nature 387: 512-516, 1997; Higashiyama et al., J. Biochem. 122: 675-680, 1997; and WO 97/09425).

By "anti-ErbB2 antibody" or "anti-HER2 antibody" is meant an antibody that specifically binds to the extracellular domain of the ErbB2 (also known as HER2 in humans) receptor and prevents the ErbB2 (HER2)-dependent signal transduction initiated by neuregulin binding.

By "transformed cell" is meant a cell (or a descendent of a cell) into which a DNA molecule encoding a neuregulin or polypeptide having a neuregulin EGF-like domain has been introduced, by means of recombinant DNA techniques or known gene therapy techniques.

By "promoter" is meant a minimal sequence sufficient to direct transcription. Also included in the invention are those promoter elements which are sufficient to render promoter-dependent gene expression controllable for cell type or physiological status (e.g., hypoxic versus normoxic conditions), or inducible by external signals or agents; such elements may be located in the 5' or 3' or internal regions of the native gene.

By "operably linked" is meant that a nucleic acid encoding a polypeptide (e.g., a cDNA) and one or more regulatory sequences are connected in such a way as to permit gene expression when the appropriate molecules (e.g., transcriptional activator proteins) are bound to the regulatory sequences.

By "expression vector" is meant a genetically engineered plasmid or virus, derived from, for example, a bacteriophage, adenovirus, retrovirus, poxvirus, herpesvirus, or artificial chromosome, that is used to transfer a polypeptide (e.g., a neuregulin) coding sequence, operably linked to a promoter, into a host cell, such that the encoded peptide or polypeptide is expressed within the host cell.

BRIEF DESCRIPTION OF THE DRAWINGS

FIGS. 8A and 8B are representations of photomicrographs showing that GGF2 induces hypertrophic growth of neonatal rat ventricular myocytes.

FIG. 8C is a representation of a Northern blot, showing that prepro-atrial natriuretic factor (prepro-ANF), a marker of ventricular hypo trophy, and α-skeletal actin are up-regulated in neonatal rat ventricular myocytes treated with GGF2.

FIG. 8D is a graph showing that GGF2 stimulates protein synthesis (indicated by relative $^3$H-leucine uptake) in neonatal rat ventricular myocytes.

DETAILED DESCRIPTION OF THE INVENTION

Figure 1A:
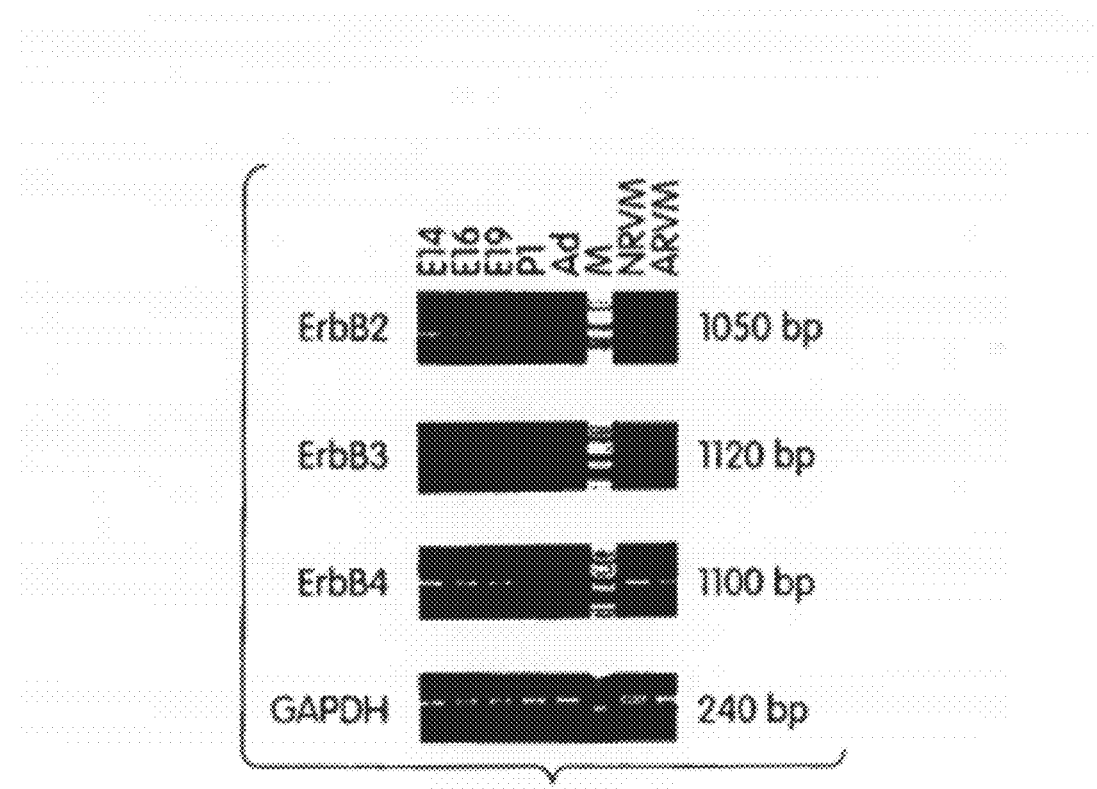
FIG. 1A is a representation of a semiquantitative RT-PCR analysis showing expression of neuregulin receptors during cardiac development and in adult rat cardiomyocytes.

We have found that neuregulins promote survival and hypertrophic growth of cultured cardiac myocytes through activation of ErbB2 and ErbB4 receptors.

In addition, we have observed, in animals with experimentally-induced intracardiac pressure overload, that cardiomyocyte ErbB2 and ErbB4 levels are normal during early compensatory hypertrophy and decrease during the transition to early heart failure.

Together, our in vitro and in vivo findings show that neuregulins are involved in stimulating compensatory hypertrophic growth in response to increased physiologic stress, as well as inhibiting apoptosis of myocardial cells subjected to such stress. These observations indicate that neuregulin treatment will be useful for preventing, minimizing, or reversing congestive heart disease. While not wishing to be bound by theory, it is likely that neuregulin treatment will strengthen the pumping ability of the heart by stimulating cardiomyocyte hypertrophy, and will partially or completely inhibit further deterioration of the heart by suppressing cardiomyocyte apoptosis.

Neuregulins

Polypeptides encoded by the NRG-1, NRG-2, and NRG-3 genes possess EGF-like domains that allow them to bind to and activate ErbB receptors. Holmes et al. (*Science* 256: 1205-1210, 1992) has shown that the EGF-like domain alone is sufficient to bind and activate the p185erbB2 receptor. Accordingly, any polypeptide product encoded by the NRG-1, NRG-2, or NRG-3 gene, or any neuregulin-like polypeptide, e.g., a polypeptide having an EGF-like domain encoded by a neuregulin gene or cDNA (e.g., an EGF-like domain containing the NRG-1 peptide subdomains C-C/D or C-C/D', as described in U.S. Pat. No. 5,530,109, U.S. Pat. No. 5,716, 930, and U.S. Ser. No. 08/461,097; or an EGF-like domain as disclosed in WO 97/09425) may be used in the methods of the invention to prevent or treat congestive heart failure.

Risk Factors

Risk factors that increase the likelihood of an individual's developing congestive heart failure are well known. These include, and are not limited to, smoking, obesity, high blood pressure, ischemic heart disease, vascular disease, coronary bypass surgery, myocardial infarction, left ventricular systolic dysfunction, exposure to cardiotoxic compounds (alcohol, drugs such as cocaine, and anthracycline antibiotics such as doxorubicin, and daunorubicin), viral infection, pericarditis, myocarditis, gingivitis, thyroid disease, genetic defects known to increase the risk of heart failure (such as those described in Bachinski and Roberts, *Cardiol. Clin.* 16:603-610, 1998; Siu et al., *Circulation* 8:1022-1026, 1999; and Arbustini et al., *Heart* 80:548-558, 1998), starvation, eating disorders such as anorexia and bulimia, family history of heart failure, and myocardial hypertrophy.

Accordingly, neuregulins may be administered to prevent or decrease the rate of congestive heart disease progression in those identified as being at risk. For example, neuregulin administration to a patient in early compensatory hypertrophy may permit maintenance of the hypertrophic state and may prevent the progression to heart failure. In addition, those identified to be at risk, as defined above, may be given cardioproctive neuregulin treatment prior to the development of compensatory hypertrophy.

Neuregulin administration to cancer patients prior to and during anthracycline chemotherapy or anthracyclinelanti-ErbB2 (anti-HER2) antibody (e.g., HERCEPTIN®) combination therapy may prevent the patients' cardiomyocytes from undergoing apoptosis, thereby preserving cardiac function. Patients who have already suffered cardiomyocyte loss may also derive benefit from neuregulin treatment, because the remaining myocardial tissue will respond to neuregulin exposure by displaying hypertrophic growth and increased contractility.

Therapy

Neuregulins and polypeptides containing EGF-like domains encoded by neuregulin genes may be administered to patients or experimental animals with a pharmaceutically-acceptable diluent, carrier, or excipient, in unit dosage form. Conventional pharmaceutical practice may be employed to provide suitable formulations or compositions to administer such compositions to patients or experimental animals. Although intravenous administration is preferred, any appropriate route of administration may be employed, for example, parenteral, subcutaneous, intramuscular, intracranial, intraorbital, ophthalmic, intraventricular, intracapsular, intraspinal, intracisternal, intraperitoneal, intranasal, aerosol, oral, or topical (e.g., by applying an adhesive patch carrying a formulation capable of crossing the dermis and entering the bloodstream) administration. Therapeutic formulations may be in the form of liquid solutions or suspensions; for oral administration, formulations may be in the form of tablets or capsules; and for intranasal formulations, in the form of powders, nasal drops, or aerosols. Any of the above formulations may be a sustained-release formulation.

Methods well known in the art for making formulations are found in, for example, "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Sustained-release, biocoinpatible, biodegradable lactide polymer, lactideiglycolide copolymer, or polyoxyethylene-polyoxypropylene copolymers may be used to control the release of the compounds. Other potentially useful parenteral delivery systems for administering molecules of the invention include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Gene Therapy

Neuregulins and neuregulin-like polypeptides containing neuregulin EGF-like domains may also be administered by somatic gene therapy. Expression vectors for neuregulin gene therapy (e.g., plasmids, artificial chromosomes, or viral vectors, such as those derived from adenovirus, retrovirus, poxvirus, or herpesvirus) carry a neuregulin-encoding (or neuregulin-like polypeptide-encoding) DNA under the transcriptional regulation of an appropriate promoter. The promoter may be any non-tissue-specific promoter known in the art (for example, an SV-40 or cytomegalovirus promoter). Alternatively, the promoter may be a tissue-specific promoter, such as a striated muscle-specific, an atrial or ventricular cardiomyocyte-specific (e.g., as described in Franz et al., *Cardiovasc. Res.* 35:560-566, 1997), or an endothelial cell-specific promoter. The promoter may be an inducible promoter, such as the ischemia-inducible promoter described in Prentice et al. (*Cardiovasc. Res.* 35:567-574, 1997). The promoter may also be an endogenous neuregulin promoter.

The expression vector may be administered as naked DNA mixed with or conjugated to an agent to enhance the entry of the DNA into cells, e.g., a cationic lipid such as Lipofectin™, Lipofectamine™ (Gibco/BRL, Bethesda, Md.), DOTAP™ (Boeringer-Mannheim, Indianapolis, Ind.) or analogous compounds, liposomes, or an antibody that targets the DNA to a particular type of cell, e.g., a cardiomyocyte or an endothelial cell. The method of administration may be any of those described in the Therapy section above. In particular, DNA for somatic gene therapy has been successfully delivered to the heart by intravenous injection, cardiac perfusion, and direct injection into the myocardium (e.g., see Losordo et al., *Circulation* 98:2800-2804, 1998; Lin et al., *Hypertension* 33:219-224, 1999; Labhasetwar et al., *J. Pharm. Sci.* 87:1347-1350, 1998; Yayama et al., *Hypertension* 31:1104-1110, 1998). The therapeutic DNA is administered such that it enters the patient's cells and is expressed, and the vector-encoded therapeutic polypeptide binds to and activates cardiomyocyte ErbB receptors.

The following Examples will assist those skilled in the art to better understand the invention and its principles and advantages. It is intended that these Examples be illustrative of the invention and not limit the scope thereof.

Example I

General Methods

Preparation of Cardiac Myocyte and Non-Myocyte Primary Cultures

Neonatal rat ventricular myocyte (NRVM) primary cultures were prepared as described previously (Spriughorn et al., *J. Biol. Chem.* 267: 14360-14365, 1992). To selectively enrich for myocytes, dissociated cells were centrifuged twice at 500 rpm for 5 min, pre-plated twice for 75 min, and finally plated at low density ($0.7\text{-}1\times10^4$ cells/cm$^2$) in Dulbecco's modified Eagle's (DME) medium (Life Technologies Inc., Gaithersburg, Md.) supplemented with 7% fetal bovine serum (FBS) (Sigma, St. Louis, Mo.). Cytosine arabinoside (AraC; 10 µM; Sigma) was added to cultures during the first 24-48 h to prevent proliferation of non-myocytes, with the exception of cultures used for thymidine uptake measurements. Unless otherwise stated, all experiments were performed 36-48 h after changing to a serum-free medium, DME plus ITS (insulin, transferrin, and selenium; Sigma). Using this method, we routinely obtained primary cultures with >95% myocytes, as assessed by microscopic observation of spontaneous contraction and by immunofluorescence staining with a monoclonal anti-cardiac myosin heavy chain antibody (anti-MHC; Biogenesis, Sandown, N.H.).

Primary cultures of cellular fractions isolated from neonatal hearts enriched in non-myocyte cells were prepared by twice passaging cells that adhered to the tissue culture dish during the preplating procedure. These non-myocyte cultures, which contained few antiNHC-positive cells, were allowed to grow to subconfluence in DME supplemented with 20% FBS before switching to DME-ITS for a subsequent 36 to 48 h.

Isolation and preparation of adult rat ventricular myocyte (ARVM) primary cultures was carried out using techniques previously described (Berger et al., *Am. J. Physiol.* 266: H341-H349, 1994). Rod-shaped cardiac myocytes were plated in culture medium on laminin—(10 µg/ml; Collaborative Research, Bedford, Mass.) precoated dishes for 60 min, followed by one change of medium to remove loosely attached cells. The contamination of ARVM primary cultures by non-myocytes was determined by counting with a haemocytometer and was typically less than 5%. All ARVM primary cultures were maintained in a defined medium termed "ACCITT" (Ellingsen et al., *Am. J. Physiol.* 265: H747-H754, 1993) composed of DME, supplemented with 2 mg/ml BSA, 2 mM L-carnitine, 5 mM creatine, 5 mM taurine, 0.1 µM insulin, and 10 nM triiodothyronine with 100 IU/ml penicillin and 100 µg/ml streptomycin. In experimental protocols designed to examine myocyte survival and/or apoptosis, insulin was omitted from the defined medium, which is therefore termed "ACCTT".

PCR Analysis of ErbB Receptors in Rat Heart cDNA sequences encoding portions of the C-termini of ErbB receptors were amplified by using the following synthetic oligonucleotide primers: ErbB2A (5'-TGTGCTAGT-CAAGAGTCCCAACCAC-3': sense; SEQ ID NO: 1) and ErbB2B (5'-CCTTCTCTCGGTAC TAAGTATTCAG-3': antisense; SEQ ID NO: 2) for amplification of ErbB2 codon positions 857 to 1207 (Bargmann et al., *Nature* 319: 226-230, 1986); ErbB3A (5'-GCTTAAAGTGCTTGGCTCGGGT-GTC-3: sense; SEQ ID NO: 3) and ErbB3B (5'-TCCTACA-CACTGACACTTTCTCTT-3': antisense; SEQ ID NO: 4) for amplification of ErbB3 codon positions 712 to 1085 (Kraus et al., *Proc. Natl. Acad. Sci. USA* 86: 9193-9197, 1989); ErbB4A (5'-AATTCACCCATCAGAGTGACGTTTGG-3: sense; SEQ ID NO: 5) and ErbB4B (5'-TCCTGCAGG-TAGTCTGGGTGCTG: antisense; SEQ ID NO: 6) for amplification of ErbB4 codon positions 896 to 1262 (Plowman et al., *Proc. Natl. Acad. Sci. USA* 90: 1746-1750, 1993), RNA samples (1 µg) from rat hearts or freshly isolated neonatal and adult rat ventricular myocytes were reverse-transcribed to generate first-strand cDNA. The PCR reactions were performed in a final volume of 50 µl containing approximately 50 ng of first-strand cDNAs for thirty cycles in a PTC-100™ Programmable Thermal Controller (MJ Research, Inc.; Watertown, Mass.). Each cycle included 30 sec at 94° C., 75 sec at 63° C., and 120 sec at 72° C. Thirty µl aliquots of each reaction mixture were analyzed by electrophoresis in 1% agarose gels and by ethidium bromide staining. The PCR products were directly cloned into the TA cloning vector (Invitrogen Co., San Diego, Calif.) and verified by automatic DNA sequencing.

Analysis of ErbB Receptor Phosphorylation

To analyze which receptor subtypes were tyrosine-phosphorylated, neonatal and adult ventricular myocyte cells were maintained in serum-free medium for 24 to 48 h, and then treated with recombinant human glial growth factor 2 (rhGGF2) at 20 ng/ml for 5 min at 37° C. Cells were quickly rinsed twice with ice-cold phosphate-buffered saline (PBS) and lysed in cold lysis buffer containing 1% NP40, 50 mM Tris-HCl (pH 7.4), 150 mM NaCl, 1 mM ethylene glycol-bis (β-aminoethyl ether)-N,N,N',N'-tetraacetic acid (EGTA), 1 mM ethylenediaminetetraacetic acid (EDTA), 0.5% sodium deoxycholate, 0.1% SDS, 1 mM sodium orthovanadate, 10 mM sodium molybdate, 8.8 g/L sodium pyrophosphate, 4 g/L NaFl, 1 mM phenylmethylsulfonyl fluoride (PMSF), 10 µg/ml aprotinin, and 20 µM leupeptin. Lysates were centrifuged at 12,000×g at 4° C. for 20 min, and aliquots of 500 µg (neonatal myocytes) or 2000 µg (adult myocytes) of supernatant were incubated with antibody specific to ErbB2 or ErbB4 (Santa Cruz Biotechnology Inc., Santa Cruz, Calif.) overnight at 4° C. and precipitated with protein A-agarose (Santa Cruz Biotechnology, Inc.). Immunoprecipitates were collected and released by boiling in sodium dodecyl sulfate (SDS) sample buffer. Samples were fractionated by SDS-polyacrylamide gel electrophoresis (SDS-PAGE), transferred to polyvinylidene difluoride (PVDF) membranes (Biorad Laboratories, Hercules, Calif.) and probed with a PY20 antiphosphotyrosine antibody (Santa Cruz Biotechnology, Inc.). For detection of ErbB2, the supernatants were also immunoprecipitated with a biotinylated RC20 antiphosphotyrosine antibody (Upstate Biotechnology, Inc., Lake Placid, N.Y.) and blotted with a monoclonal antibody to ErbB2 (Ab-2; Oncogene Research Products, Cambridge, Mass.).

Incorporation of [$^3$H]Thymidine and [$^3$H]Leucine

As an index of DNA synthesis, [$^3$H]thymidine incorporation was measured as described previously (Berk et al., *Hypertension* 13:305-314, 1989). After incubation for 36 to 48 h in serum-free medium (DME plus ITS), the cells were stimulated with different concentrations of rhGGF2 (Cambridge NeuroScience Co., Cambridge, Mass.) for 20 h. [$^3$H]thymidine (0.7 Ci/mmol; Dupont) was then added to the medium at a concentration of 5 µCi/ml and the cells were cultured for another 8 h. Cells were washed with PBS twice, 10% TCA once, and 10% TCA was added to precipitate protein at 4° C. for 45 min. Parallel cultures of myocytes not exposed to rhGGF2 were harvested under the same conditions as controls. The precipitate was washed twice with 95% ethanol, resuspended in 0.15 N NaOH and saturated with 1 M HCl, then aliquots were counted in a scintillation counter. The results are expressed as relative cpm/dish normalized to the mean cpm of control cells in each experiment. For antibody blocking experiments, the same procedure was applied except that the cells were preincubated with an antibody (0.5 g/ml) specific for each neuregulin receptor (c-neu Ab-2, Oncogene Research Products; and ErbB3 or ErbB4, Santa Cruz Biotechnology), for 2 h prior to addition of either rhGGF2 or rhFGF2.

The rate of [$^3$H]leucine uptake was used as an index of protein synthesis. For these experiments, 10 µM cytosine arabinoside was added to the culture medium. Cells were grown in serum-free medium for 36 to 48 h and then stimulated with different doses of rhGGF2. After 40 h, [$^3$H]leucine (5 µCi/ml) was added for 8 h, and cells were washed with PBS and harvested with 10% TCA. TCA-precipitable radioactivity was determined by scintillation counting as above.

5-Bromo-2'-Deoxy-Uridine Incorporation and Immunofluorescence Staining

Nuclear 5-bromo-2'-deoxy-uridine (BrdU) incorporation and a cardiac muscle-specific antigen, myosin heavy chain (MHC), were simultaneously visualized using double-indirect immunofluorescence. Primary NRVM cultures were maintained in DME plus ITS for 48 h and then stimulated with rhGGF2 (40 ng/ml) for 30 h. Control cultures were prepared similarly but without rhGGF2. BrdU (10 µM) was added for the last 24 h. Cells were fixed in a solution of 70% ethanol in 50 mM glycine buffer, pH 2.0, for 30 min at −20° C., rehydrated in PBS and incubated in 4 N HCl for 20 min. Cells were then neutralized with three washes in PBS, incubated with 1% FBS for 15 min, followed by a mouse monoclonal anti-MHC (1:300; Biogenesis, Sandown, N.H.) for 60 min at 37° C. The primary antibody was detected with TRITC-conjugated goat anti-mouse IgG (1:300, The Jackson Laboratory, Bar Harbor, Me.), and nuclear BrdU incorporation was detected with fluorescein-conjugated anti-BrdU antibody from an in situ cell proliferation kit (Boehringer Mannheim Co. Indianapolis, Ind.). The coverslips were mounted with Flu-mount (Fisher Scientific; Pittsburgh, Pa.), and examined by immunofluorescence microscopy. About 500 myocytes were counted in each coverslip and the percentage of BrdU-positive myocytes was calculated.

For examination of changes in myocyte phenotype with rhGGF2, cells were fixed in 4% (w/v) paraformaldehyde for 30 min at room temperature, rinsed with PBS, permeabilized with 0.1% Triton X-100 for 15 min, and then incubated with 1% FBS for another 15 min, followed by incubation with anti-MHC (1:300) and visualized with TRITC-conjugated (NRVM) or FITC-conjugated (ARVM) second antibody. ARVM were examined using a MRC 600 confocal microscope (BioRad; Hercules, Calif.) with a Kr/Ar laser.

Cell Survival Assay and Detection of Apoptosis

Cell viability was determined by the 3-(4,5-dirnethylthiazol-2-yl)-2,5-diphenyl tetrazolium bromide (MTT, Sigma) cell respiration assay, which is dependent on mitochondrial activity in living cells (Mosman, *J. Immunol. Meth.* 65:55-63, 1983). Primary cultures of NRVM after 2 days in serum-free medium were stimulated with different concentrations of rhGGF2 for either 4 or 6 days. ARVM were maintained in ACCTT medium or ACCTT medium plus different concentrations of rhGGF2 for 6 days. MTT was then incubated with the cells for 3 h at 37° C. Living cells transform the tetrazolium ring into dark blue formazan crystals that can be quantified by reading the optical density at 570 nm after cell lysis with dimethylsulfoxide (DMSO; Sigma).

Apoptosis was detected in neonatal and adult myocytes using the terminal deoxynucleotidyltransferase (TdT)-mediated dUTP nick end-labeling (TUNEL) assay. 3'-end labelling of DNA with fluorescein-conjugated dUTP was done using an in situ cell death detection kit (Boehringer Mannheim, Indianapolis, Ind.) following the manufacturer's instructions. Cells were counterstained with an anti-MHC antibody as described above, and the nuclei were also stained with Hoescht 33258 (10 µM, Sigma) for 5 min. More than 500 myocytes were counted in each coverslip and the percentage of TUNEL positive myocytes was calculated.

Flow cytometric analysis of neonatal myocytes fixed in 70% ethanol/PBS and stained with propidium iodide was also performed to quantify the percentage of cells undergoing apoptosis. This method is based upon the observation that cells undergoing apoptosis have a hypo-diploid quantity of DNA and localize in a broad area below the G0/G1 peak on a DNA histogram. Briefly, cells were collected by trypsinization, pooled with nonattached cells, and fixed in 70% ethanol. After being rinsed once with PBS, cells were incubated with a propidiurn iodide (20 µg/ml, Sigma) solution containing RNase A (5 Kunitz units/ml) at room temperature for 30 min. Data were collected using a FACScan (Becton-Dicicinson, San Jose, Calif.). For each sample, 10,000 events were collected. Aggregated cells and extremely small cellular debris were gated out.

Isolation and Hybridization of RNA

Total cellular RNA was isolated by a modification of the acid guanidinium/thiocyanate phenol/chloroform extraction method (Chomczynski and Sacchi, *Anal. Biochem.* 162:156-159, 1987) using the TRIZOL reagent (Life Technologies Inc., Gaithersburg, Md.). RNA was size-fractionated by formaldehyde agarose gel electrophoresis, transferred to nylon filters (Dupont, Boston, Mass.) by overnight capillary blotting and hybridized with cDNA probes labelled with [$\alpha$-$^{32}$P]dCTP by random priming (Life Technologies Inc.). The filters were washed under stringent conditions and exposed to X-ray film (Kodak X-Omat AR, Rochester, N.Y.). Signal intensity was determined by densitometry (Ultrascan XL, Pharmacia). The following cDNA probes were used: rat preproatrial natriuretic factor (prepro-ANF; a marker of cardiomyocyte hypertrophy) (0.6 kb of coding region) (Seidman, et al., *Science* 225:324-326, 1984), and rat skeletal $\alpha$-actin (240 bp of a 3'-untranslated region) (Shani et al.,

*Nucleic Acids Res.* 9:579-589, 1981). A rat glyceraldehyde-3-phosphate dehydrogenase (GAPDH; a housekeeping gene) cDNA probe (240 bp of the coding region) (Tso et al., *Nucleic Acids Res.* 13:2485-2502, 1985) was used as control for loading and transfer efficiency.

Aortic Stenosis Model

Ascending aortic stenosis was performed in male Wistar weanling rats (body weight 50-70 g, 3-4 weeks, obtained from Charles River Breeding Laboratories, Wilmington, Mass.), as previously described (Schunkert et al., *Circulation,* 87:1328-1339, 1993; Weinberg et al. *Circulation,* 90:1410-1422, 1994; Feldman et al., *Circ. Res.,* 73:184-192, 1993; Schunkert et al., *J. Clin. Invest.* 96:2768-2774, 1995; Weinberg et al., *Circulation,* 95:1592-1600, 1997; Litwin et al., *Circulation,* 91:2642-2654; 1995). Sham-operated animals served as age-thatched controls. Aortic stenosis animals and age-matched sham-operated controls were sacrificed after anesthesia with intraperitoneal pentobarbital 65 mg/kg at 6 and 22 weeks after surgery (n=20-29 per group). Hemodynamic and echocardiographic studies in this model have shown that compensatory hypertrophy with normal left ventricular (LV) cavity dimensions and contractile indices is present 6 weeks after banding, whereas animals develop early failure by 22 weeks after banding, which is characterized by onset of LV cavity enlargement and mild depression of ejection indices and pressure development per gram LV mass. In the present study, in vivo LV pressure measurements were perfomed prior to sacrifice as previously described (Schunkert et al., *Circulation,* 87:1328-1339, 1993; Weinberg et al. *Circulation,* 90:1410-1422, 1994; Feldman et al., *Circ. Res.,* 73:184-192, 1993; Schunkert et al., *J. Clin. Invest.* 96:2768-2774, 1995; Weinberg et al., *Circulation,* 95:1592-1600, 1997; Litwin et al., *Circulation,* 91:2642-2654; 1995). The animals were also inspected for clinical markers of heart failure, including the presence of tachypnea, ascites, and pleural effusions. Both body weight and LV weight were recorded.

LV Myocyte Isolation for RNA Extraction

In a subset of animals (n=10 per group), the heart was rapidly excised and attached to an aortic cannula. Myocyte dissociation by collagenase perfusion was performed as previously described (Kagaya et al., *Circulation,* 94:2915-2922, 1996; Ito et al., *J. Clin. Invest.* 99:125-135, 1997; Tajima et al., *Circulation,* 99:127-135, 1999). To evalutate the percentage of myocytes in the final cell suspension, aliquots of myocytes were fixed, pee ineabilized and blocked. The cell suspension was then incubated with antibodies against α-sarcomeric actin (mAb, Sigma, 1:20) and von Willebrand Factor (pAb, Sigma, 1:200) to distinguish between myocytes and endothelial cells. Secondary antibodies (goat anti-rabbit, goat anti-mouse pAb, Molecular probes, 1:400) with a Texas Red (or Oregon Green) conjugate were used as a detection system. Ninety-eight percent myocytes and less than 2% fragments of endothelial cells or unstained cells (fibroblasts) were routinely obtained.

RNA Analysis

Total RNA was isolated from control and hypertrophied myocytes (n=10 hearts in each group), and from LV tissue (n=10 hearts in each group) using TRI Reagent (Sigma). Tissue and myocyte RNA were used for the following protocols. Using myocyte RNA, Northern blots were used to assess message levels of atrial natriuretic peptide which were normalized to GAPDH (Feldman et al., *Circ. Res.* 73:184-192, 1993; Tajima et al., *Circulation,* 99:127-135, 1999). These experiments were done to confirm the specificity of myocyte origin of the RNA using this molecular marker of hypertrophy.

We also performed reverse transcription-polymerase chain reactions (RT-PCRs) for initial estimation of the presence of ErbB2, Erb134 and neuregulin in samples derived from adult rat heart and adult myocytes using the following pairs of primers: ErbB2 sense 5' GCT GGC TCC GAT GTA TTT GAT GGT 3' (SEQ ID NO: 7), ErbB2 antisense 5' GTT CTC TGC CGT AGG TGT CCC TTT 3' (SEQ ID NO: 8) (Sarkar et al., *Diagn. Mol. Pathol.* 2:210-218, 1993); ErbB3 sense 5' GCT TAA AGT GCT TGG CTC GGG TGT C 3' (SEQ ID NO: 3), ErbB3 antisense 5' TCC TAC ACA CTG ACA CTT TCT CTT 3' (SEQ ID NO: 4) (Kraus et al., *Proc. Natl. Acad. Sci. USA* 86:9193-9197; 1989), ErbB4 sense 5' AAT TCA CCC ATC AGA GTG ACG TTT GG 3' (SEQ ID NO: 5), ErbB4 antisense 5' TCC TGC AGG TAG TCT GGG TGC TG 3' (SEQ ID NO: 6) (Plowman et al., *Proc. Natl. Acad. Sci. USA* 90:1746-1750; 1993); neuregulin sense 5' GCA TCA CTG GCT GAT TCT GGA G 3' (SEQ ID NO: 9), neuregulin antisense 5' CAC ATG CCG GTT ATG GTC AGC A 3' (SEQ ID NO: 10). The latter primers recognize nucleic acids encoded by the NRG-1 gene, but do not discriminate between its isoforms. The amplification was initiated by 1 min of denaturation, 2 min of annealing at the gene specific temperature and 2 min extension at 72° C. The whole PCR reaction was electrophoresed on a 1% agarose gel and the PCR products of expected size were gel-purified.

After cloning these fragments into pGEM-T vector (Promega, Madison, Wis.), the correctness and orientation of those fragments within the vector was confirmed by sequencing. Cloned PCR fragments were used to generate a radiolabeled riboprobe using the MAXIscript in vitro transcription kit (Ambion, Inc., Austin, Tex.) and $\alpha$-$^{32}$P-UTP. The plasmids containing the ErbB2, ErbB4 or neuregulin fragment were linearized and a radiolabeled probe was synthesized by in vitro transcription with T7 or T3 RNA polymerase. The β-actin probe provided by the kit was transcribed with T7 or T3 polymerase and resulted in a 330 and 300 bp fragment, respectively. 20 μg of total RNA was hybridized to $5\times10^5$ cpm of ErbB2, ErbB4 or neuregulin c-RNA together with $2\times10^4$ cpm of β-actin for later normalization according to the RPA II kit (Ambion) protocol.

After digestion with RNase A/RNase T1, the samples were precipitated, dried, redissolved and finally separated on a 5% polyacrylamide gel for 2 hours. The gel was exposed to Kodak MR film for 12-48 hours, and the assay was quantified by densitometric scanning of the auto-radiograph using Image Quant software (Molecular Dynamics, Inc., Sunnyvale, Calif.). ErbB2, ErbB4 and neuregulin mRNA levels were normalized to β-actin.

Western Blotting of ErbB2 and ErbB4

LV tissue (n=5 hearts per group) was rapidly homogenized in a RIPA buffer containing 50 mmol/L Tris HCl, pH 7.4, 1% NP-40, 0.1% SDS, 0.25% Na-deoxycholate, 150 mM NaCl, 1 mM EDTA, 1 mM PMSF, 1 Aprotinin, 1 μg/ml leupeptin, 1 μg/ml pepstatin and 1 mM $Na_3PO4$. Proteins were quantified using the Lowry assay kit (Sigma). 50 μg of protein in Laemmli SDS sample buffer were boiled for 5 minutes and after centrifugation loaded onto a 10% SDS-PAGE gel. After electrophoresis, proteins were transferred to a nitrocellulose membrane at 100 mA overnight. The filters were blocked with 0.05% Tween-20, 5% nonfat milk and then incubated with anti-ErbB2 or anti-ErbB4 (Santa Cruz Biotechnology, each diluted 1:100, 1 μg/ml). After incubation with goat anti-rabbit peroxidase-conjugated secondary antibody diluted 1:2000, blots were subjected to the enhanced chemiluminescent (ECL) detection method (Amersham, Life Science) and afterwards exposed to Kodak MR film for 30-180 seconds.

Protein levels were normalized to protein levels of β-actin detected with anti-β-actin (Sigma).

In Situ Hybridization for Neuregulin

10-μm cryostat sections of left ventricular tissue (n=2 control and 6-week aortic stenosis hearts) were used for in situ hybridizations. Antisense and sense RNA probe was synthesized from cDNA fragments in pBluescript with either T7 or T3 RNA polymerase and digoxigenin-labeled UTP (DIG RNA Labeling Mix, Boehringer Mannheim). Tissue sections were first treated with 4% paraformaldehyde for 20 minutes, followed by 30 minutes digestion with proteinase K (10 μg/ml) at 37° C. and another 5 minutes of fixation in 4% paraformaldehyde.

Following the fixation, the slides were washed in PBS three times for 5 minutes, after which the sections were immersed in 0.1 M triethanolamine chloride buffer with 0.25% acetic anhydride for 10 minutes to block polar and charged groups on the section and hence prevent nonspecific probe binding. After washing the slides in 2×SSC, they were then prehybridized (50% formamide, 2×SSC, 5% dextransulfate, 0.1% SDS, 1×Denhardt's, 400 μg/ml denatured salmon sperm DNA) at 45° C. for 60 minutes in a moist chamber charged with 50% formamide/2×SSC. After 1 hour, the probes were added to the prehybridization solution and the slides were hybridized for 16-18 hours at 45° C.

Following overnight hybridization, slides were twice washed in 4×SSC for 30 minutes at 45° C. while shaking, and then incubated with RNaseA (40 μg/ml) in 500 mM NaCl, 10 mM Tris, 1 mM EDTA, pH 8.0, for 30 minutes at 37° C. to remove unhybridized probe. After RNase treatment, sections were immersed in 2×SSC at 50° C. for 30 minutes and then in 0.2×SSC at the same temperature for another 30 minutes. The slides were equilibrated with TBS I buffer (100 mM Tris, 150 mM NaCl pH 7.5) and then blocked with blocking reagent for 30 minutes at room temperature according to the manufacturer's protocol (DIG Nucleic Acid Detection Kit, Boehringer Mannheim).

After removing the blocking reagent, the slides were immersed in TBS I for 1 minute and then the anti-DIG-AP conjugate solution (DIG Nucleic Acid Detection Kit, Boehringer Mannheim) was applied to each section for 1.5 hours at room temperature in a humid chamber. Afterwards, the slides were washed in TBS I three times, 10 minutes per wash, to wash off the excess antibody and equilibrated in TBS II (100 mM Tris, 100 mM NaCl, pH 9.5, 50 mM $MgCl_2.7H_2O$) for 5 minutes. The color substrate was prepared according to the manufacturer's instructions and applied to each section until a blue-colored reaction became visible. The reaction was stopped and the slides were washed in PBS and distilled water for 5 minutes each. After a nuclear counter-staining the sections were dehydrated through an ethanol series, immersed in xylene and mounted by cover-slipping in Permount.

Statistical Analysis

All values are expressed as mean±SEM. Statistical analysis of differences observed between the aortic stenosis groups (6 and 22 weeks after banding) and the age-matched control groups was done by ANOVA comparison. An unpaired Student's test was used for comparison among the groups at the same age post-banding. Statistical significance was accepted at the level of $p<0.05$.

Example II

Neuregulins Promote Survival and Growth of Cardiac Myocytes

Expression of Neuregulin Receptors in the Heart

To determine which of the NRG receptors (i.e., ErbB2, ErbB3, ErbB4) are expressed in rat myocardium, RNA from rat heart tissues at successive stages of development, and from freshly isolated neonatal and adult ventricular myocytes, were reverse-transcribed and amplified by PCR, using primers that flank the variable C-termini of ErbB receptors. FIG. 1A shows the semiquantitative RT-PCR analysis of neuregulin receptor mRNA levels during cardiac development. Total RNA from embryonic (E14, E16, and E19), neonatal (P1) or adult (Ad) rat heart, and from freshly isolated neonatal rat ventricular myocytes (NRVM) or adult rat ventricular myocytes (ARVM) was reverse-transcribed into cDNA and amplified with receptor isoform-specific primers (see Methods). GAPDH was used as a control for reverse transcription, PCR amplification, and gel loading ("M" denotes 1 kb or 120 by DNA molecular weight standards). The RT-PCR products were verified by DNA sequencing.

All three ErbB receptors were expressed in the developing rat heart at mid-embryogenesis (E14), with the following rank order of their relative mRNA abundances: ErbB4>ErbB2>ErbB3. The expression of ErbB receptors was down-regulated later in embryogenesis. At E16 and E19, and at post-natal day 1 (P1), only ErbB2 and ErbB4 mRNAs could be detected. In adult rat heart, ErbB4 was still detectable, but its mRNA abundance was lower than that detected in embryonic and neonatal hearts, whereas ErbB2 mRNA and, rarely, ErbB3 mRNA could be detected only at low levels in adult myocardium. In freshly isolated neonatal and adult rat ventricular myocyte primary cultures, both ErbB2 and ErbB4 mRNA were readily detectable by RT-PCR, although ErbB4 expression levels were consistently higher than those of ErbB2, Furthermore, when using receptor-specific cDNA probes for ErbB2, ErbB3 and ErbB4, only transcripts for ErbB4 were readily detectable in freshly isolated neonatal and adult rat ventricular myocytes by Northern blot.

Figure 1B:
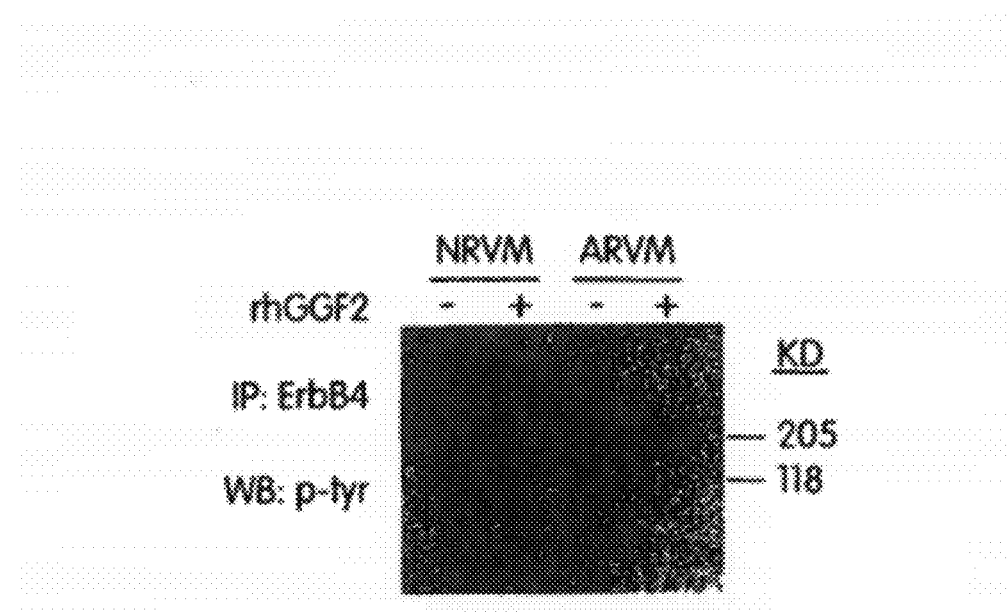
FIG. 1B is a representation of an assay showing tyrosine phosphorylation of the ErbB4 receptor in cardiomyocytes treated with recombinant human glial growth factor 2 (rhGGF2).

To determine which of the ErbB receptors were tyrosine-phosphorylated following neuregulin treatment, primary cultures of NRVM or ARVM, maintained in serum-free medium for 24 to 48 h, were treated either with or without neuregulin, i.e., recombinant human glial growth factor 2 (rhGGF2) (20 ng/ml) for 5 min. ErbB4 receptor protein was immunoprecipitated with an anti-ErbB4 antibody from 500 μg of NRVM lysates or 2000 μg of ARVM lysates, and phosphorylated form of ErbB4 was detected by an anti-phosphotyrosine antibody. The blot shown in FIG. 1B is representative of 3 independent experiments. As shown in FIG. 1B, phosphorylated ErbB4 is quite prominent in neonatal myocytes and less robust, but detectable, in adult myocytes, which is consistent with the levels of ErbB4 mRNA abundance we observed above. Phosphorylated forms of ErbB2 and ErbB3 could not be detected even if immunoprecipitated with biotinylated-antiphosphotyrosine antibody, consistent with the much-reduced mRNA abundances for these two neuregulin receptors in post-natal cardiac myocytes.

GGF2 Stimulates DNA Synthesis in Neonatal Rat Ventricular Myocytes

To investigate the ability of GGF2 to stimulate DNA synthesis in NRVM primary cultures, myocytes maintained in serum-free medium for 2 days were subsequently treated with 40 ng/ml rhGGF2 for 30 h. DNA synthesis was monitored by measuring the incorporation of either BrdU (FIG. 2B) or [$^3$H]thymidine (FIGS. 3A and 3B), which were added to the media either 24 h or 8 h, respectively, before termination of each experiment.

Figure 2A:
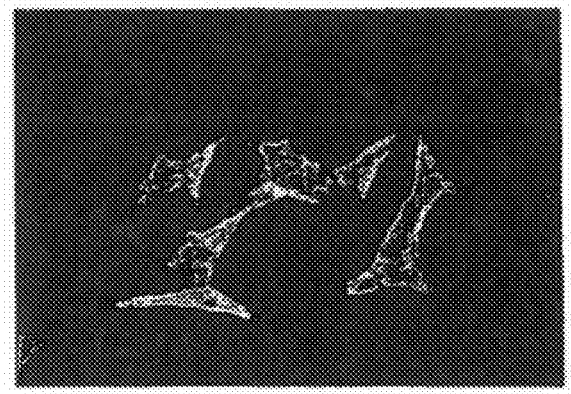
FIGS. 2A and 2B are representations of photomicrographs showing staining of neonatal rat ventricular myocytes for myosin heavy chain (FIG. 2A) and BrdU-positive nuclei (FIG. 2B).
Figure 2B:
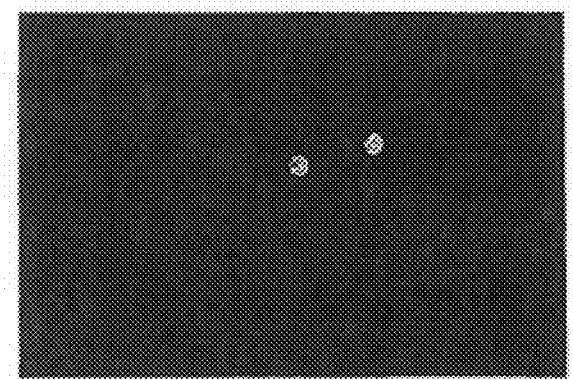
Figure 2C:
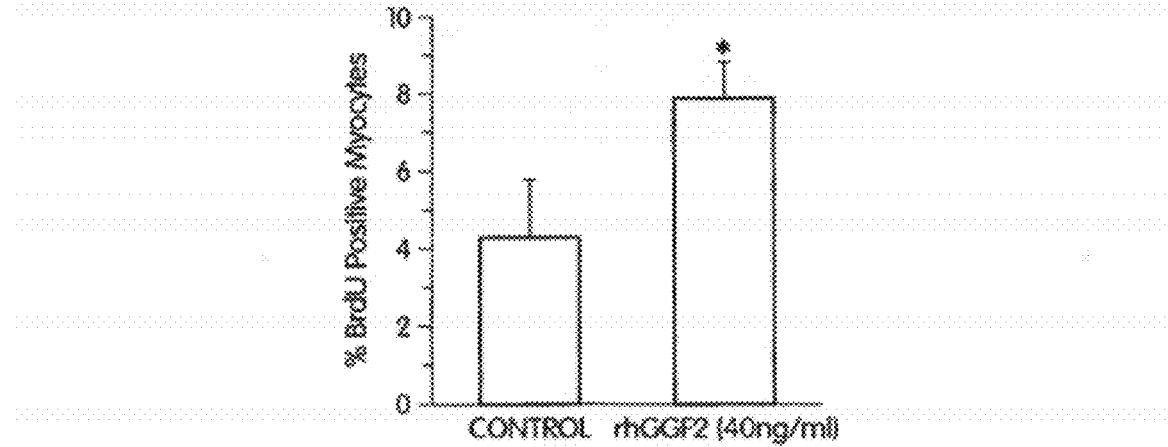
FIG. 2C is a graph showing that rhGGF2 stimulates DNA synthesis (indicated by % BrdU-positive myocytes) in neonatal rat ventricular myocytes.

FIG. 2A shows myocyte myosin heavy chain in NRVM, visualized with a TRITC-conjugated goat anti-mouse antibody (red). FIG. 2B shows BrdU-positive nuclei visualized with a fluorescein-conjugated mouse anti-BrdU antibody (green). The scale bar for FIGS. 2A and 2B is equivalent to 10 μm. FIG. 2C shows the percentage of BrdU-positive myocytes under control conditions and in the presence of GGF2 (data are mean±SD for 3 experiments. *, p<0.01), As displayed in FIG. 2C, 40 ng/ml (approximately 0.7 nM) of rhGGF2 increased the percentage of BrdU-labelled myocytes (from postnatal day 1 rat heart ventricles) by about 80%, an increase in magnitude that was similar to that observed with [$^3$H]thymidine incorporation (FIG. 3A).

Figure 3A:
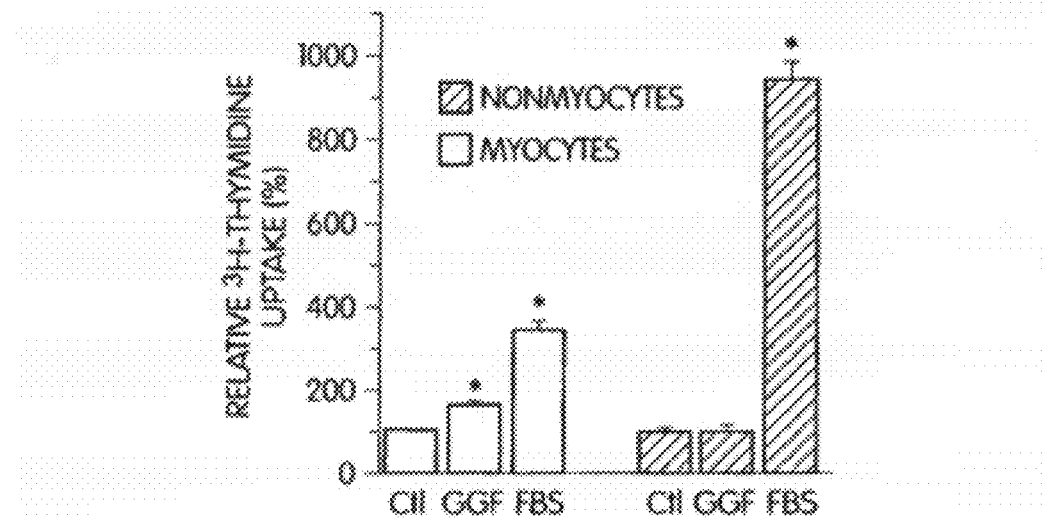
FIGS. 3A and 3B are graphs showing that rhGGF2 stimulates DNA synthesis (indicated by % relative $^3$H-thymidine uptake) in neonatal rat ventricular myocytes.
Figure 3B:
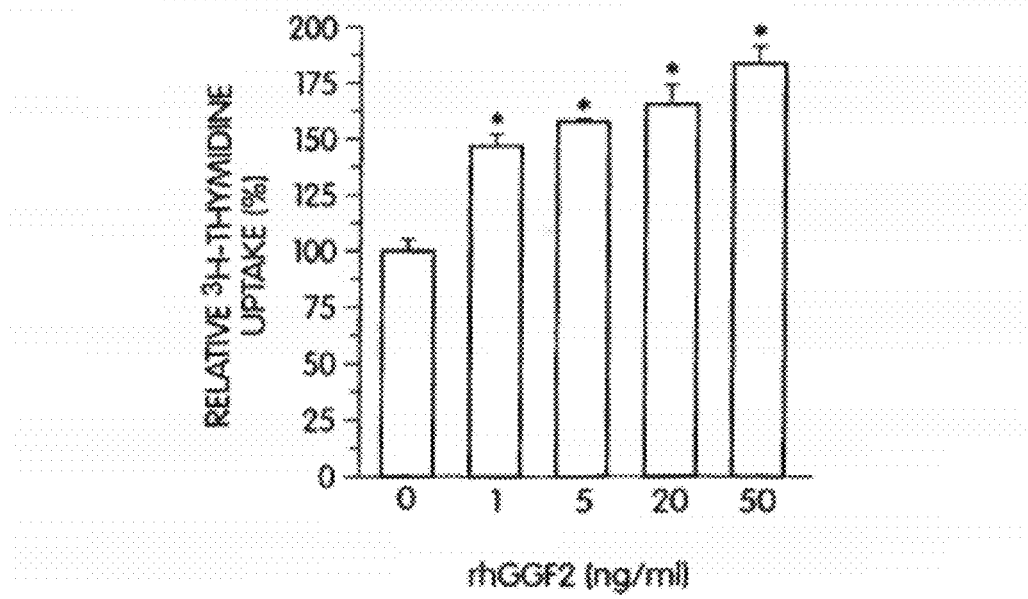

FIGS. 3A and 3B show the effects of GGF2 on DNA synthesis in myocyte-enriched and non-myocyte fractions from rat ventricular myocyte primary isolates. In FIG. 3A, NRVM-enriched primary isolates or a "non-myocyte"-enriched fraction (see Methods) were exposed to control (i.e., serum-free) medium alone (Ctl) or to medium containing either 40 ng/ml rhGGF2 (GGF) or 7% fetal bovine serum (FBS). In FIG. 3B, concentration-dependent effect of GGF2 on NRVM DNA synthesis is shown. DNA synthesis was assessed by [$^3$H]thymidine incorporation, and the data are expressed as relative cpm/dish normalized to the mean cpm of control cells in each experiment (mean±SD of triplicate analyses from three independent experiments; *, p<0.01 vs control). Twenty ng/ml of rhGGF2 provoked an approximate 60% increase in [$^3$H]thymidine incorporation into NRVM, which was about half that observed with 7% FBS. The mitogenic effect of rhGGF2 on NRVM was concentration-dependent, with about an 80% increase at 50 ng/ml (i.e., 0.9 nM) (FIG. 3B). GGF2 had similar mitogenic effects on BrdU or [$^3$H]thymidine incorporation on rat embryonic ventricular myocytes (E19) and postnatal ventricular myocytes (P5), whereas concentrations of GGF2 as high as 100 ng/ml had no effect on DNA synthesis in adult rat ventricular myocyte primary cultures.

The effects of rhGGF2 on non-myocyte fractions obtained following the preplating steps of the neonatal rat ventricular myocyte isolation procedure also were investigated. As shown in FIG. 3A, rhGGF2 did not induce any significant change in [3H]thymidine incorporation into non-myocytes. This was in contrast to 7% FBS, which induced nearly a 10-fold increase in [$^3$H]thymidine incorporation into this cell population. Therefore, GGF2 shows a relatively specific action on cardiac myocytes compared to a myocyte-depleted cell population which, using the method of myocyte isolation we employed here, is composed largely of fibroblasts and endothelial cells.

To determine which of the known neuregulin receptors mediate the mitogenic effect of GGF2 on fetal and neonatal ventricular myocytes, DNA synthesis was measured in primary NRVM cultures after incubation with antibodies specific for ErbB2, ErbB3 and ErbB4. Neonatal myocytes were cultured for two days in serum-free medium, after which they were treated for 30 h either without (control), or with rhGGF2 (10 ng/ml), or with rhFGF2 (20 ng/ml), or with GGF2/FGF2 and antibodies to ErbB2, ErbB3 or ErbB4, either alone or in combination as illustrated. Antibodies (0.5 μg/ml/antibody) were preincubated with cells for 2 h before the addition of either GGF2 or FGF2. [$^3$H]Thymidine was added during the last 8 h (data are expressed as relative cpm/dish normalized to the mean cpm of control cells in each experiment, and are presented as mean±SD; n=3 independent experiments; *, p<0.04 vs rhGGF2 alone; #, p>0.1 vs rhGGF2 alone).

Figure 4:
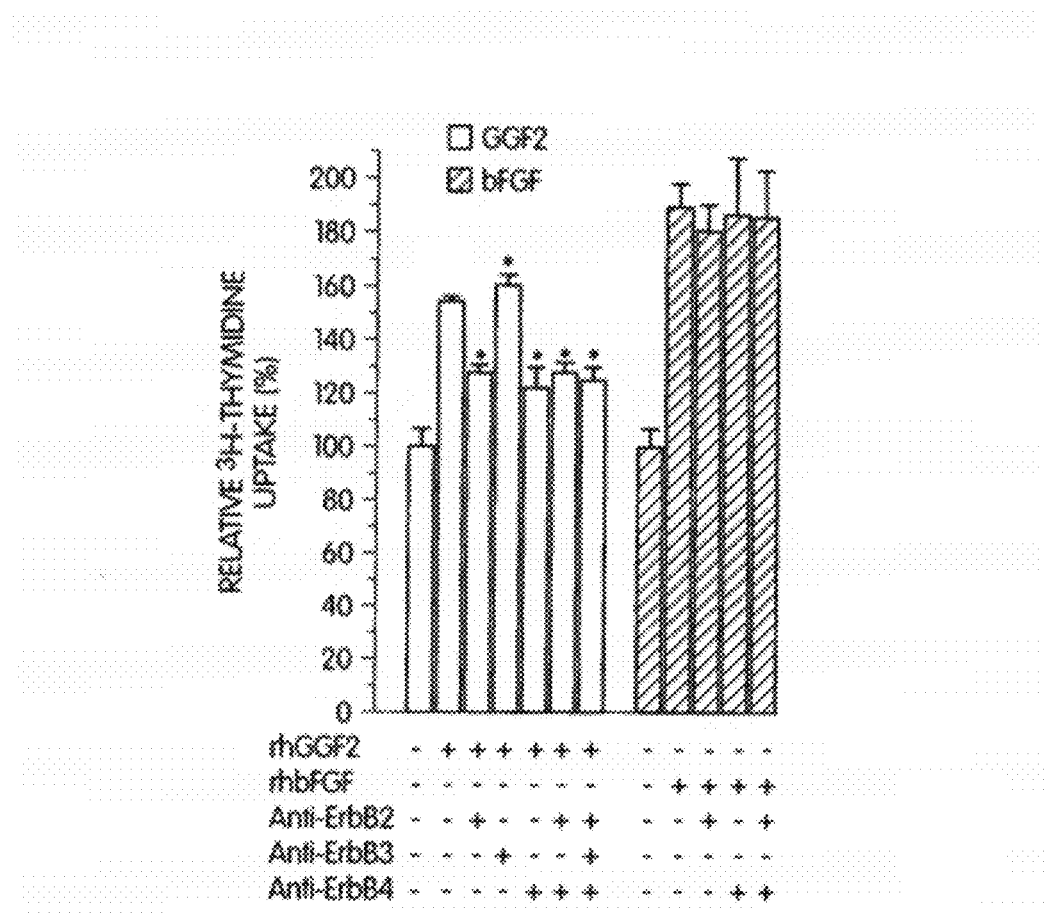
FIG. 4 is a graph showing that ErbB2 and ErbB4 mediate the effects of GGF2 on relative $^3$H-thymidine uptake in neonatal rat ventricular myocytes.

As shown in FIG. 4, a monoclonal antibody against the extracellular domain of c-neu/ErbB2, inhibited the GGF2-dependents increase in [$^3$H]thymidine incorporation into NRVM by GGF2 could be inhibited. Similarly, an antibody directed against the C-terrninus of ErbB4 also blocked about 50% of the increase in [$^3$H]thymidine incorporation induced by GGF2. A combination of these two antibodies had the same effect as either the anti-ErbB2 or anti-ErbB4 antibodies alone. In contrast, an antibody to ErbB3 had no effect on GGF2-induced DNA synthesis. To verify that the effects seen with the ErbB2 and ErhB4 antibodies were specific for GGF, sister NRVM primary cultures were treated with 20 ng/ml rhFGF2 (recombinant human bFGF). Neither antibody had any effect on the approximately 2-fold increase in [$^3$H]thymidine incorporation with rhFGF2. These results suggest that at least two of the known neuregulin receptor tyrosine kinases were present and coupled to downstream signalling cascades in the neonatal ventricular myocyte.

GGF2 Promotes Cardiac Myocyte Survival In Vitro

Figure 5:
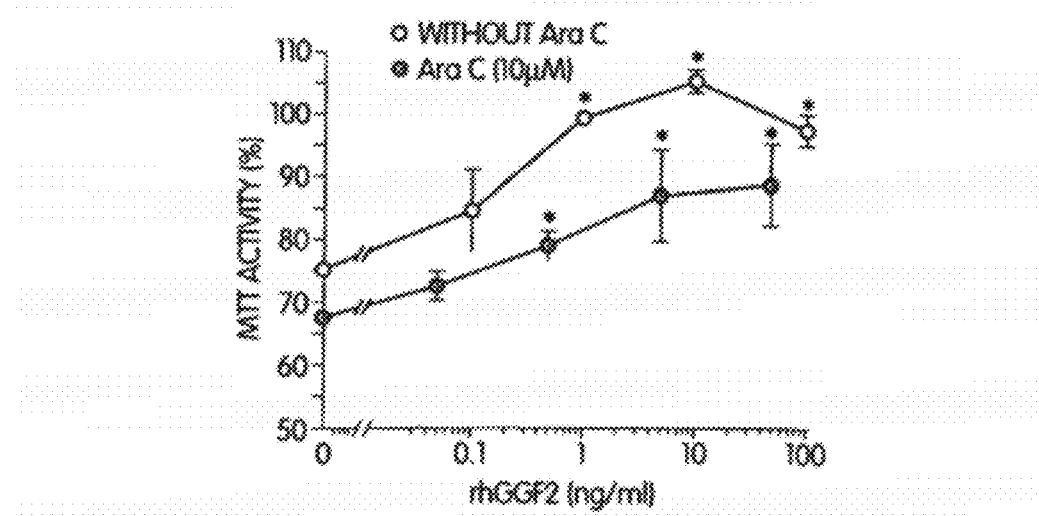
FIG. 5 is a graph showing that GGF2 promotes survival in primary cultures of neonatal rat ventricular myocytes.

During development, the net increase in the number of functional embryonic myocytes is dependent on both myocyte proliferative capacity and survival. Therefore, it was of interest to determine whether GGF2 could promote survival of cardiac myocytes in addition to proliferation. Primary cultures of NRVM maintained in serum-free medium, with or without 10 μM of cytosine arabinoside (AraC), were treated with the indicated concentrations of GGF2 for 4 days, and the relative numbers of metabolically active cells were determined by a MTT cell respiration assay (see Methods). Data are expressed as a percentage of the mean MTT activity of myocytes in triplicate culture dishes on day 0 at the time of the addition of GGF2. Data are shown as mean±SD (n=3 experiments; *, p<0.05 vs control). We observed that approximately 25% of cells die by day 4. In contrast, addition of GGF2 resulted in a 30% increase in MTT activity compared to controls. The effect was concentration-dependent with an EC50 of 0.2 ng/ml (FIG. 5). This survival effect was observed in NRVM primary cultures for up to 7 days; it was also observed in the presence of cytosine arabinoside (AraC), an antiproliferative agent. As shown in FIG. 5, the survival effect of GGF2 was observed at 4 days in the continuous presence of cytosine arabinoside, with about 90% myocyte viability in the presence of 50 ng/ml rhGGF2 compared to approximately 70% viability in control cultures. In contrast, GGF2 had no significant effect on the survival of myocyte-depleted, "non-myocyte"-enriched primary isolates at 4 days.

Figure 6A:
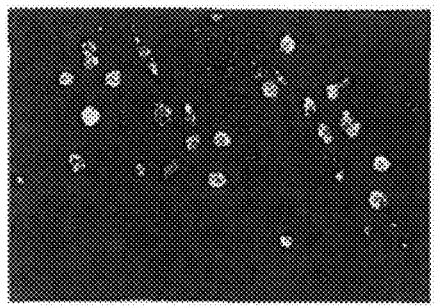
FIGS. 6A-6C and 6E-6G are representations of photomicrographs showing that GGF2 diminishes apoptotic cell death in primary cultures of neonatal rat ventricular myocytes.
Figure 6E:
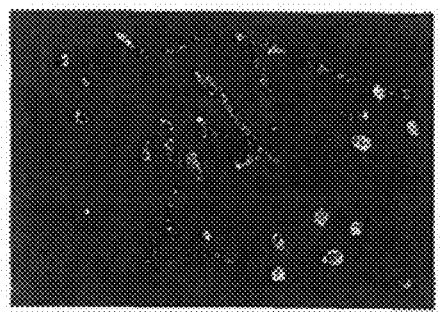
Figure 6B:
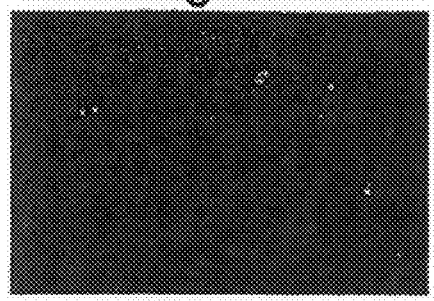
Figure 6F:
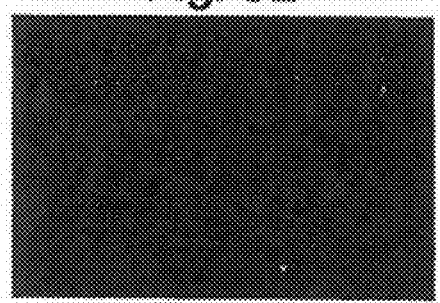
Figure 6C:
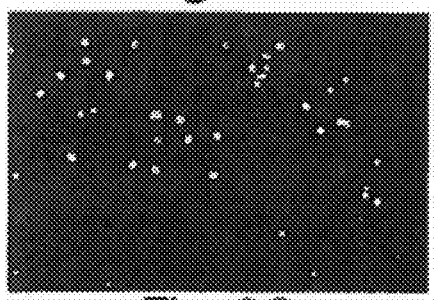
Figure 6G:
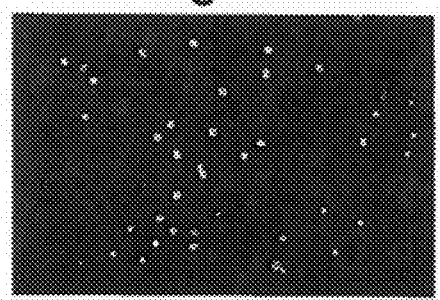
Figure 6D:
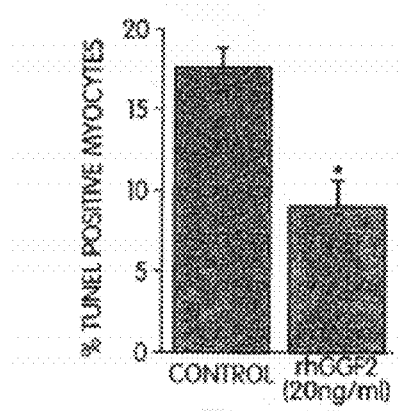
FIG. 6D is a graph showing that rhGGF2 diminishes apoptotic cell death in primary cultures of neonatal rat ventricular myocytes (indicated by a decrease in the percentage of TUNEL-positive myocytes).
Figure 6H:
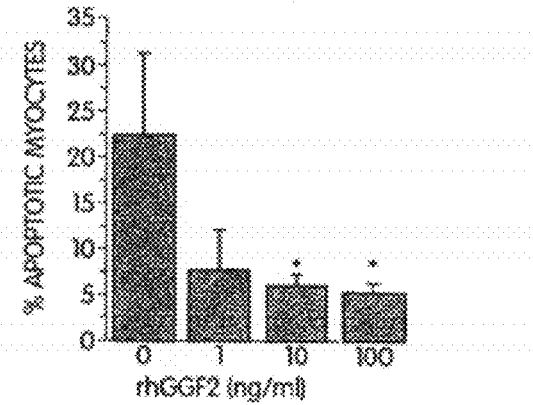
FIG. 6H is a graph showing that rhGGF2 diminishes apoptotic cell death in primary cultures of neonatal rat ventricular myocytes (determined by flow cytometry analysis of the sub-G1 fraction following propidium iodide staining of rhGGF2-treated cells).

We examined next whether the survival effect of GGF2 was mediated by inhibition of programmed cell death (apoptosis). Primary cultures of NRVM 2 days in serum-free medium were maintained in either the absence of rhGGF2 (FIGS. 6A-6C) or in the presence of 20 ng/ml of rhGGF2 (FIGS. 6E-6G) for 4 days. Cells were then fixed and stained with anti-MHC antibody and a TRITC-conjugated secondary antibody to visualize myocytes (FIGS. 6A and 6E) or with fluorescein-conjugated dUTP (i.e., TUNEL) to reveal apoptotic cells (FIGS. 6B and 6F). The TUNEL-positive myocytes displayed cell shrinkage and chromatin condensation, which were also identified by Hoescht 33258-staining (FIGS. 6C and 6G). Apoptosis was quantified either by counting the number of TUNEL-positive myocytes (FIG. 6D) or by flow cytometry analysis of the sub-G1 fraction following propidium iodine-staining of primary NRVM cultures that had been treated for 4 days with the indicated concentrations of rhGGF2 (H). The data shown for FIG. 6D and FIG. 6H are given as mean±S.D for three independent experiments. The scale bar in FIGS. 6A-6C and 6E-6G represents 10 μM.

After 6 days in serum-free medium, about 17% of NRVM maintained under control conditions at low density (i.e., sub-confluent) exhibited evidence of apoptosis as detected by TUNEL staining, with small condensed nuclei and cell shrinkage consistent with apoptotic cell death (FIGS. 6A-6C and 6E-6G). In the presence of 20 ng/ml rhGGF2, the number of TUNEL positive myocytes declined to about 8% (FIG. 6D). The effect of GGF2 on inhibiting apoptosis was also quantified using flow cytometric analysis of propidium iodide-labelled NRVM primary cultures. After 4 days in serum- and insulin-free medium, 22% of NRVM were hypodiploid, consistent with initiation of programmed cell death. In the presence of rhGGF2 at concentrations above 10 ng/ml, less than 10% of NRVM exhibited evidence of apoptosis (FIG. 6H).

Figure 7A:
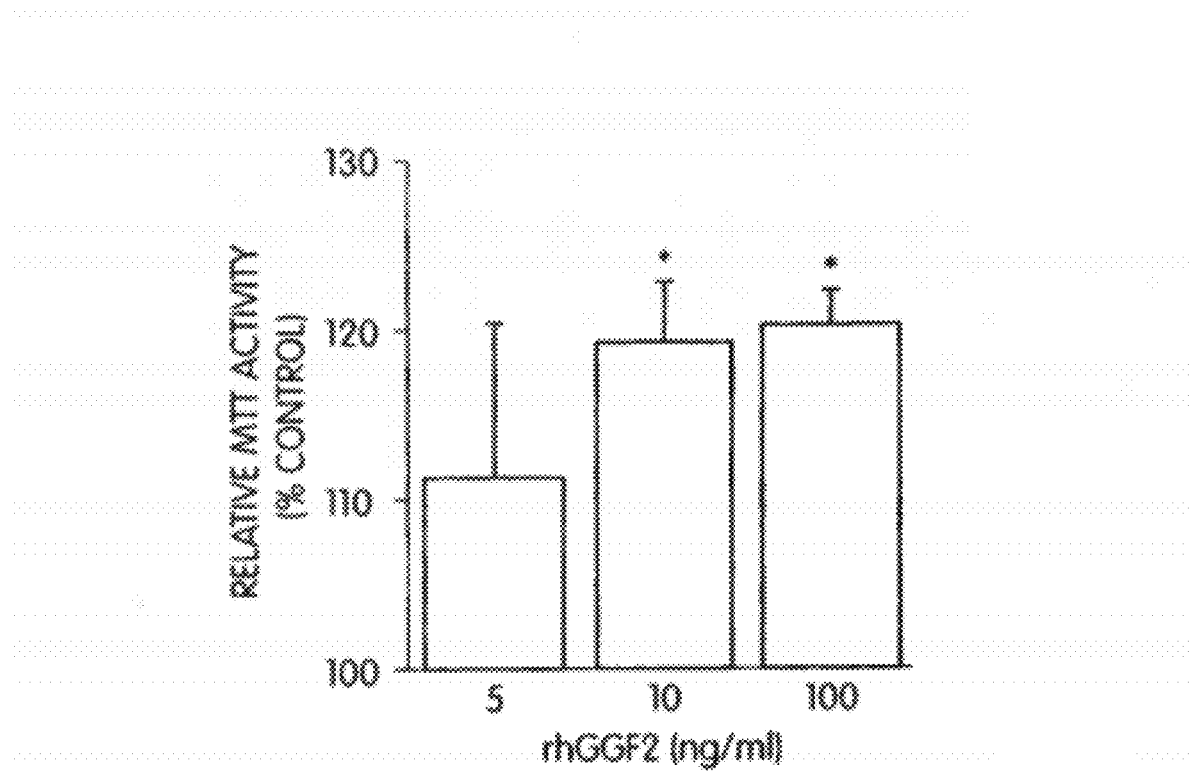
FIGS. 7A and 7B are graphs showing that rhGGF2 increases survival and decreases apoptotic cell death in primary cultures of adult rat ventricular myocytes.
Figure 7B:
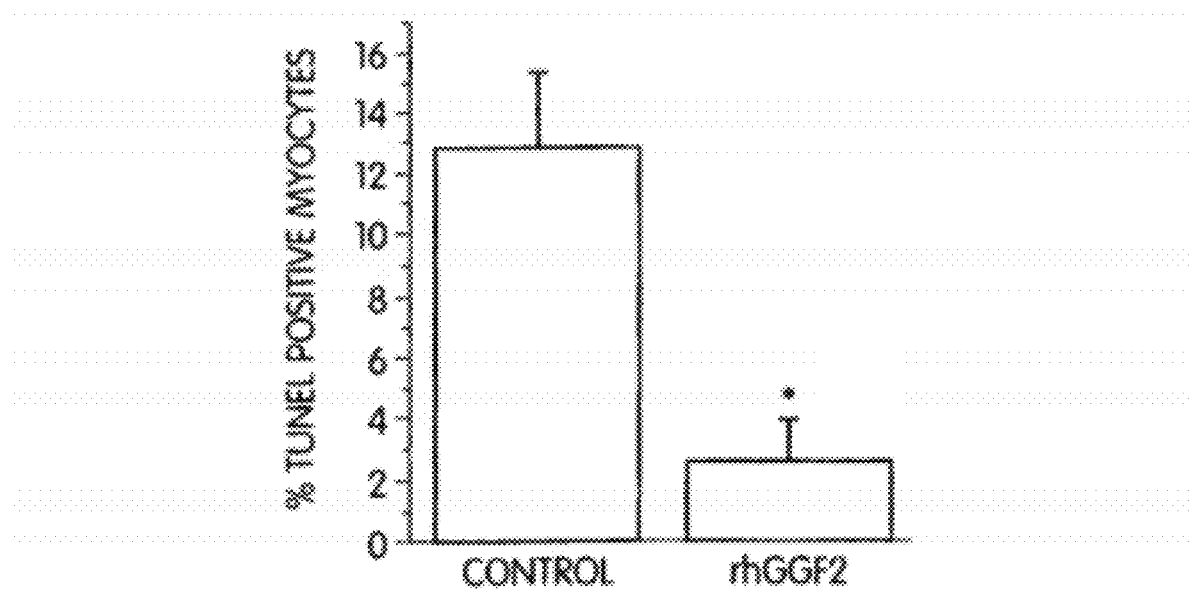

The survival and antiapoptotic effects of GGF2 on the adult rat ventricular myocyte (ARVM) were also examined by MTT cell respiration assay and TUNEL staining. In the experiment shown in FIG. 7A, primary cultures of ARVM were maintained in either a serum- and insulin-free medium "ACCTT", see Methods), or ACCTT medium plus GGF2 for 6 days. The number of metabolically active cells was determined by the MTT cell respiration assay, and the data are expressed as the relative absorbance normalized to the mean absorbance of untreated, control cells. Each bar represents the mean±S.D (n=3 experiments; *, p<0.05 vs control). In the experiment shown in FIG. 7B, primary cultures of ARVM were maintained in ACCTT medium (control) or ACCTT medium plus rhGGF2 (25 ng/ml) for 3 days. After fixation with 4% paraformaldehyde, myocytes were visualized with an anti-MHC antibody and a TRITC-conjugated secondary antibody, and apoptotic cells were identified by TUNEL staining. About 500 myocytes were counted on each coverslip (data are mean±S.D of three independent experiments; p<0.05 versus control). When compared to untreated ARVM primary cultures, in which more than 10% of cells were positive for TUNEL labelling, rhGGF2 (20 ng/ml)-treated adult myocyte cultures exhibited only about 3% TUNEL-positive staining (FIG. 7B). These results indicate neuregulins act as survival factors at least in part by preventing programmed cell death in both neonatal and adult ventricular myocytes.

GGF2 Induces Hypertrophic Growth of Cardiac Myocytes

In order to investigate whether neuregulin signalling can induce a hypertrophic (growth) response in cardiac myocytes, we examined the effects of GGF2 on induction of myocyte hypertrophy in both neonatal and adult rat ventricular myocyte primary cultures. FIGS. 8A and 8B show photomicrographs of subconfluent NRVM primary isolates incubated either without (FIG. 8A) or with (FIG. 8B) rhGGF2 (20 ng/ml) for 72 h in serum-free medium, after which cells were fixed and stained with an antibody to cardiac MHC (red, TRITC) and examined using indirect immunofluorescence microscopy. The scale bar shown in the figure represents 10 μM. After a 72-hr incubation in serum-free medium with 20 ng/ml (i.e., 0.36 nM) of rhGGF2, neonatal cardiac myocytes (NRVM) exhibited a significant increase in cell size and in myofibrillar development.

A hypertrophic response in cardiac myocytes is characterized by a number of phenotypic changes in addition to an increase in cell size, such as an increase in contractile protein content without cellular proliferation and the re-activation of an "embryonic" gene program. Therefore, we examined the effects of neuregulin on levels of prepro-ANF and skeletal α-actin mRNA (transcripts normally found in relatively low abundance in neonatal and adult ventricular myocytes), and on [$^3$H]leucine incorporation as an index of protein synthesis in NRVM primary cultures. FIG. 8C shows a Northern blot analysis for prepro-ANF and skeletal α-actin mRNA from total RNA (20 μg/lane) from NRVM incubated either with or without rhGGF2 (20 ng/ml) for the times indicated. Equal loading and transfer of RNA were confirmed by GAPDH hybridization. RhGGF2 (20 ng/ml) increased mRNA levels for prepro-ANF and skeletal-actin within 60 min, approximately doubling by 16 h.

To test the effect of GGF2 on protein synthesis, NVRM were cultured in serum free medium for 24 h, after which they were treated with the indicated concentrations of rhGGF2 for 40 h, and pulsed with [$^3$H]leucine for 8 h before termination of GGF2 stimulation. The incorporation of [$^3$H]leucine at each concentration of GGF2 was normalized to the protein content of each dish, and data are expressed as relative cpm/dish normalized to the mean cpm of untreated control cells in each experiment (mean±S.D.; n=3 experiments; *, p<0.01 vs control). FIG. 8D shows that GGF2 also stimulated [$^3$H] leucine incorporation, with about a 120% increase at 48 h, at a concentration of 5 ng/ml. To minimize possible confounding effects of GGF2 on the rate of [$^3$H]leucine uptake into non-myocyte contaminant cells, these experiments were repeated in the continuous presence of cytosine arabinoside with similar results.

Figures 9A, 9B, 9C:
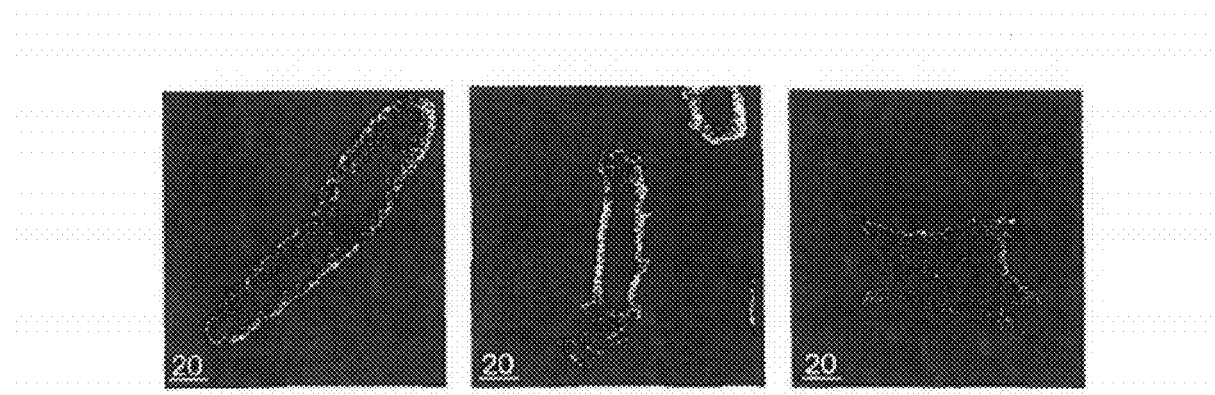
FIGS. 9A-9C are photomicrographs showing that GGF2 induces hypertrophic growth in primary cultures of adult rat ventricular myocytes.

GGF2 also caused hypertrophic responses in cultured adult rat ventricular myocytes (ARVM). Primary cultures of ARVM were plated on coverslips in 24-well dishes and maintained for 5 days in ACCITT medium either without (FIG. 9A) or with rhGGF2 (20 ng/ml) (FIGS. 9B and 9C). Cells were fixed in 4% paraformaldehyde, stained with an antibody to myosin heavy chain (green, FITC), and examined by confocal microscopy. The scale bars represent 10 μM. By 72 h in the continuous presence of 20 ng/ml of rhGGF2, some adult myocytes had begun to develop "pseudopod"-like extensions, primarily from the region of the intercalated discs, and by 5 days, more than 60% of the GGF-treated adult cardiomyocytes displayed phenotypic changes consistent with those illustrated in FIGS. 9B and 9C, whereas more than 80% of untreated ARVM maintained the phenotype exhibited in FIG. 9A.

Figure 9D:
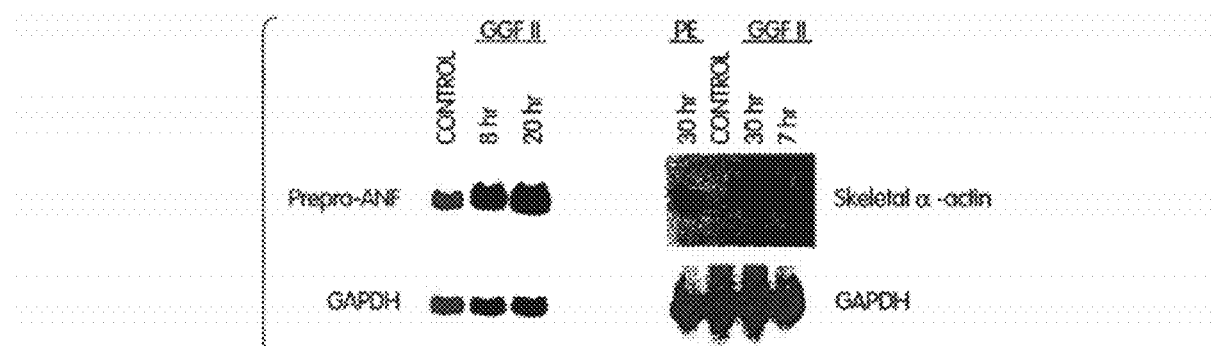
FIG. 9D is a representation of Northern blots showing that prepro-ANF and α-skeletal actin are up-regulated in adult rat ventricular myocytes treated with GGF2.

GGF2 also enhanced expression of prepro-ANF and skeletal α-actin in ARVM. Primary isolates of ARVM were stimulated either with or without 20 ng/ml rhGGF2 for the times indicated. Total RNA was isolated and analyzed by Northern blot (25 μg/lane) using prepro-ANF and skeletal α-actin cDNA probes. Equal loading and transfer conditions were confirmed by GAPDH hybridization. Phenylephrine (PE, 10 μM) was used as a positive control for hypertrophic growth. As shown in FIG. 9D, rhGGF2 (20 ng/ml) doubled prepro-ANF mRNA abundance in ARVM primary cultures after 8 h, and this had increased 3- to 4-fold within 20 h. An increase in skeletal α-actin mRNA abundance was also observed that was greater than that seen with phenylephrine (10 μM), an α-adrenergic agonist known to induce hypertrophic growth and reexpression of a number of fetal genes in adult rat ventricular myocytes. Within 7 h, skeletal α-actin mRNA levels were easily detectable, and increased by an additional 250% by 30 h treatment with GGF2. Neither GGF2 nor phenylephrine had any effect on GAPDH mRNA abundance under the conditions employed here.

Figure 9E:
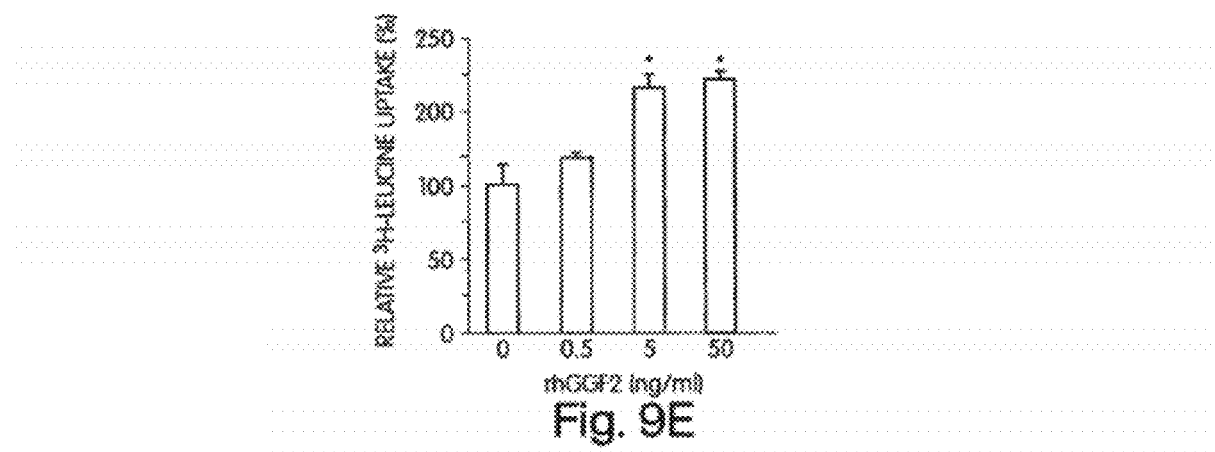
FIG. 9E is a graph showing that GGF2 stimulates protein synthesis (indicated by relative $^3$H-leticine uptake) in adult rat ventricular myocytes.

To test the effect of GGF2 on protein synthesis, ARVM (2 days in ACCITT medium) were stimulated with increasing concentrations of rhGGF2 for 40 h and [$^3$H]leucine was added during the last 14 h. [$^3$H]Leucine uptake in GGF2-treated cultures was normalized to the mean of [$^3$H]-leucine uptake in non-stimulated control myocytes. Data were also normalized to protein content of each dish to adjust for any variability in cell number among dishes (mean±SD; n=4; *, p<0.01 vs control). As illustrated in FIG. 9E, GGF2 induced a dose-dependent increase in [$^3$H]leucine incorporation, with a 70% increase at a concentration of 5 ng/ml. Thus, this neuregulin induces phenotypic changes consistent with hypertrophic adaptation in both neonatal and adult rat ventricular myocyte phenotypes at subnanomolar concentrations.

Example III

ErbB2 and ErbB4 Expression Levels Decrease in Aortic Stenosis Rats in Transition from Chronic Hypertrophy to Early Heart Failure LV Hypertrophy and Hemodynamics As shown in Table 1, left ventricular (LV) weight and the LV/body weight ratio were significantly ($p<0.05$) increased in the 6-week and 22-week aortic stenosis animals compared with age-matched controls. The in vivo LV systolic pressure was significantly increased in both 6-week and 22-week aortic stenosis animals compared with age-matched controls. In vivo LV end-diastolic pressure was also higher in aortic stenosis animals compared to age-matched controls. Consistent with prior studies in this model, LV systolic developed pressure per gram was significantly higher in 6-week aortic stenosis animals in comparison with age-matched controls, but depressed in 22-week aortic stenosis animals. At 22-week post banding, the aortic stenosis animals also showed clinical markers of failure including tachypnea, small pleural and pericardial effusions.

TABLE 1

Left Ventricular Hypertrophy and Hemodynamics

|  | C (6 wks) | LVH (6 wks) | C (22-wks) | LVH (22 wks) |
|---|---|---|---|---|
| BW (g) | 397 ± 10 | 378 ± 15 | 590 ± 10 | 564 ± 19 |
| LV Wt (g) | 1.25 ± 0.05 | 1.58 ± 0.06* | 1.64 ± 0.07 | 2.46 ± 0.10* |
| LV Wt/BW (g/kg) | 3.18 ± 0.13 | 4.40 ± 0.21* | 2.84 ± 0.14 | 4.41 ± 0.20* |
| LVEDP (mmHg) | 4.8 ± 0.3 | 12.4 ± 0.7* | 6.5 ± 0.8 | 15.7 ± 1.0* |
| LVSP (mmHg) | 104 ± 3 | 181 ± 7* | 129 ± 5 | 182 ± 9* |
| LVdevP/g (mmHg/g) | 84.2 ± 5.2 | 108.1 ± 6.8* | 82.4 ± 7.8 | 68.1 ± 4.2*_ |

Table 1 Legend:
LVH, hearts with left ventricular hypertrophy, 6 and 22 weeks after aortic stenosis;
C, age-matched controls;
BW, body weight;
LV Wt, left ventricular weight;
LVEDP, LV end-diastolic pressure;
LVSP, LV systolic pressure;
LV devP, LV developed pressure per gram.
Values are mean ± SEM;
*$p < 0.05$ vs. age-matched controls;
_ $p < 0.05$ vs. 6-weeks LVH.
n = 14-20 per group.

Expression of LV ErbB2, ErbB4 and Neuregulin in Aortic Stenosis

Figure 10A:
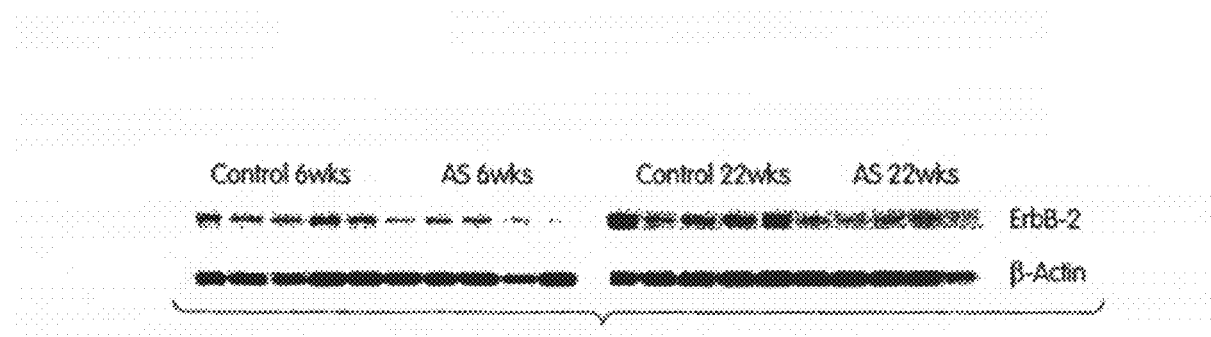
FIGS. 10A and 10B are representations of ribonuclease protection assays showing expression levels of ErbB2 (FIG. 10A), ErbB4 (FIG. 10B), and β-actin in the left ventricles of control and aortic stenosis rat hearts.
Figure 10B:
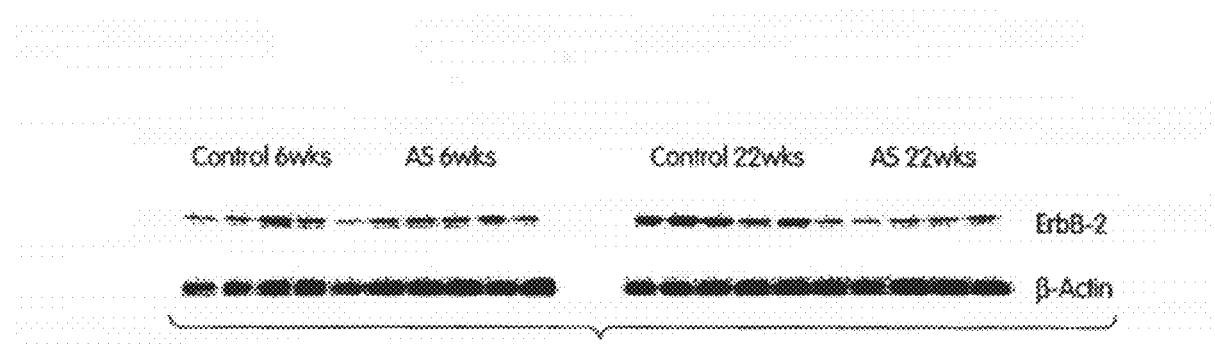

Using RT-PCR, we were able to detect ErbB2, ErbB4 and neuregulin mRNA, but not ErbB3 mRNA, in LV tissue derived from hearts of adult male rats with and without left ventricular hypertrophy, as well as in normal and hypertrophied myocytes. FIG. 10A shows a ribonuclease protection assay demonstrating LV ErbB2 and β-actin mRNA expression in 6-week aortic stenosis hearts and controls, and in 22-week aortic stenosis hearts and controls. FIG. 10B shows a ribonuclease protection assay demonstrating LV ErbB4 and β-actin mRNA expression in 6-week aortic stenosis hearts and controls, and 22-week aortic stenosis hearts and controls. Steady state levels of ErbB2, ErbB4 and neuregulin mRNA levels in LV tissue from aortic stenosis rats and controls (n=5 hearts per group) were then measured by ribonuclease protection assay (RPA) and normalized to β-actin. The LV neuregulin mRNA levels were not significantly different in tissue from 6-week aortic stenosis rats compared to age-matched controls (0.68±0.12 vs. 0.45±0.12 units, NS) or 22-week aortic stenosis rats compared to age-matched controls (0.78±0.21 vs. 0.51±0.21 units, NS). Moreover, the LV ErbB2 and ErbB4 mRNA levels, which were normalized to levels of β-actin, were preserved in 6-week aortic stenosis rats with compensatory hypertrophy relative to controls. In contrast, LV ErbB2 ($p<0.05$) and ErbB4 ($p<0.01$) message levels were significantly depressed in 22-week aortic stenosis rats at the stage of early failure (FIG. 10 and Table 2).

TABLE 2

LV mRNA and Protein Levels of ErbB Receptors

|  | C (6 wks) | LVH (6 wks) | C (22-wks) | LVH (22 wks) |
|---|---|---|---|---|
| mRNA (LV) |  |  |  |  |
| ErbB2 | 0.354 ± 0.016 | 0.326 ± 0.028 | 0.528 ± 0.072 | 0.301 ± 0.027* |
| ErbB4 | 1.158 ± 0.036 | 1.088 ± 0.062 | 1.236 ± 0.050 | 0.777 ± 0.082** |
| mRNA (myocyte) |  |  |  |  |
| ErbB2 | 0.755 ± 0.066 | 0.683 ± 0.027 | 1.609 ± 0.089 | 0.493 ± 0.035** |
| ErbB4 | 0.291 ± 0.024 | 0.266 ± 0.012 | 0.346 ± 0.023 | 0.182 ± 0.014** |

TABLE 2-continued

LV mRNA and Protein Levels of ErbB Receptors

|  | C (6 wks) | LVH (6 wks) | C (22-wks) | LVH (22 wks) |
|---|---|---|---|---|
| protein (LV) | | | | |
| ErbB2 | 1.228 ± 0.107 | 1.073 ± 0.092 | 1.218 ± 0.198 | 0.638 ± 0.065* |
| ErbB4 | 2.148 ± 0.180 | 1.968 ± 0.150 | 1.446 ± 0.119 | 0.828 ± 0.068** |

Table 2 Legend:
LVH, hearts with left ventricular hypertrophy, 6 and 22 weeks after aortic stenosis;
C, age-matched controls;
left ventricular (LV) mRNA levels were measured by ribonuclease protection assay and normalized to β-actin;
mRNA levels were measured in RNA from both LV tissue (mRNA, LV;
n = 5 hearts per group) and from LV myocytes (mRNA, myocyte;
ErbB2 n = 5 hearts per group;
ErbB4 n = 3-4 hearts per group).
LV protein levels were measured in LV tissue (n = 5 per group) by Western blotting and normalized to β-actin.
Values are mean ± SEM;
*p < 0.05 vs. age matched controls;
**p < 0.01 vs. age-matched controls.

Figure 11:
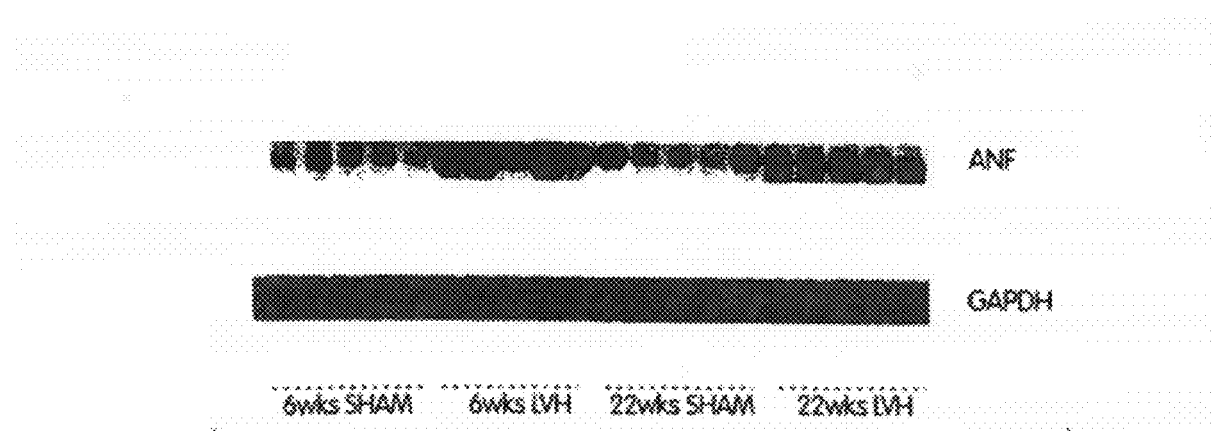
FIG. 11 is a representation of a Northern blot showing expression of ANF and glyceraldehyde phosphate dehydrogenase (GAPDH, a housekeeping gene) in myocytes from left ventricles of control and aortic stenosis rat hearts.

We next examined gene expression in RNA from LV myocytes of 6-week and 22-week aortic stenosis animals and controls. The specificity of expression in myocytes was determined by examining message levels of atrial natriuretic peptide (ANP), a positive molecular marker of pressure overload hypertrophy, using myocyte RNA and normalization to levels of GAPDH. As shown in FIG. 11, ANP was upregulated in myocytes from both 6-week (710±16 vs. 230±40 units, p<0.05) and 22-weeks aortic stenosis animals (898±52 vs. 339±13 units, p<0.05) in comparison with controls (n=5 per group). Neuregulin was not detectable by RPA in RNA derived from myocytes in any group.

Figure 12A:
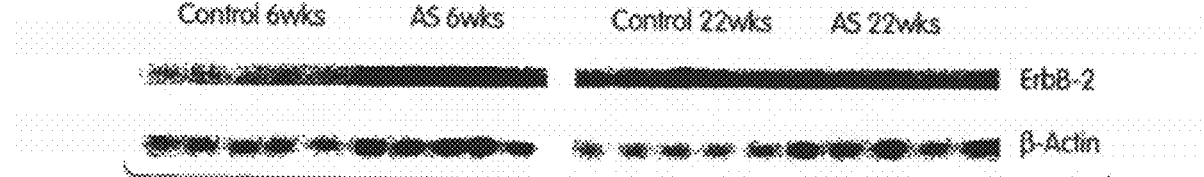
FIGS. 12A and 12B are representations of ribonuclease protection assays showing expression levels of ErbB2 (FIG. 12A), ErbB4 (FIG. 12B), and β-actin in myocytes from the left ventricles of control and aortic stenosis rat hearts.
Figure 12B:
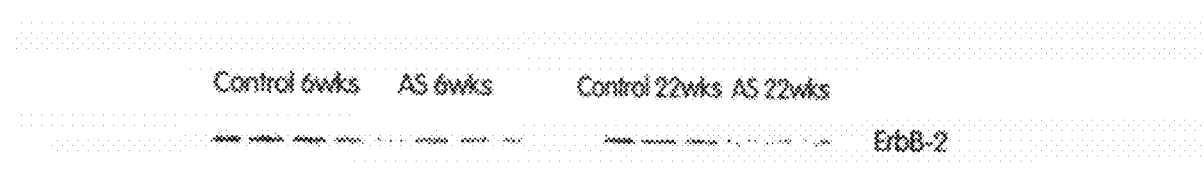

ErbB2 (n=5 per group) and ErbB4 (n=3-4 per group) message levels were also measured in myocyte RNA from both aortic stenosis groups (FIG. 12 and Table 2), FIG. 12A shows a ribonuclease protection assay demonstrating LV myocyte ErbB2 and β-actin mRNA expression in 6-weeks aortic stenosis hearts and controls, and 22-weeks aortic stenosis hearts and controls. FIG. 12B shows a ribonuclease protection assay demonstrating LV myocyte ErbB4 and β-actin mRNA expression in 6-week aortic stenosis hearts and controls, and 22-week aortic stenosis hearts and controls. Consistent with the measurements in LV tissues samples, cardiomyocyte ErbB2 and ErbB4 mRNA levels, normalized to β-actin levels, are preserved relative to controls in 6-week aortic stenosis animals at the stage of compensatory hypertrophy (NS). However, both ErbB2 and ErbB4 expression are significantly downregulated in 22-week aortic stenosis animals at the transition to failure (p<0.01).

LV ErbB2 and ErbB4 Protein Levels

Figure 13A:
FIGS. 13A and 13B are representations of a Western blot showing expression levels of ErbB2 in 6-week (FIG. 13A) and 22-week (FIG. 13B) aortic stenosis and control rat hearts.
Figure 13B:
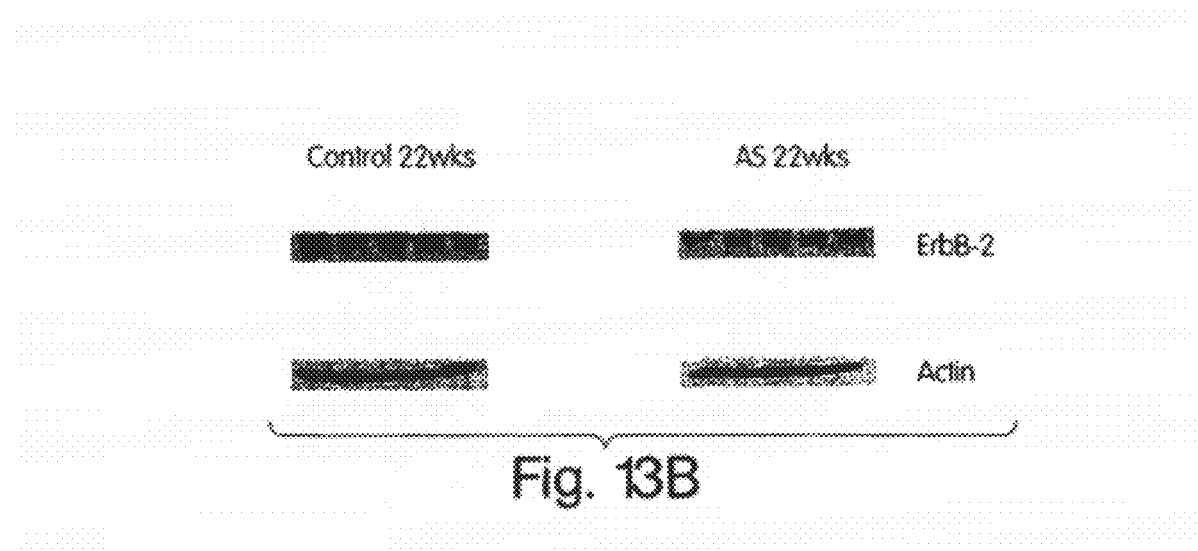
Figure 13C:
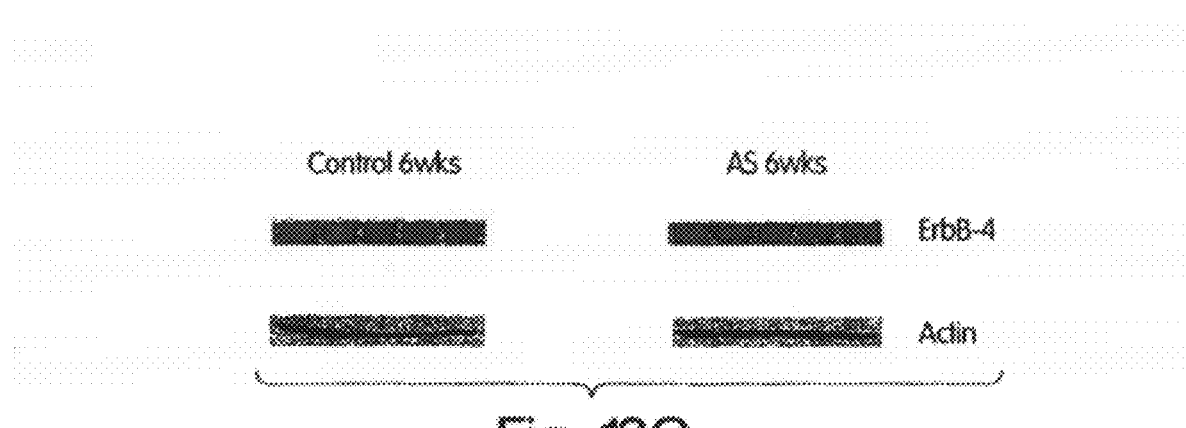
FIGS. 13C and 13D are representations of a Western blot showing expression levels of ErbB2 in 6-week (FIG. 13C) and 22-week (FIG. 13D) aortic stenosis and control rat hearts.
Figure 13D:
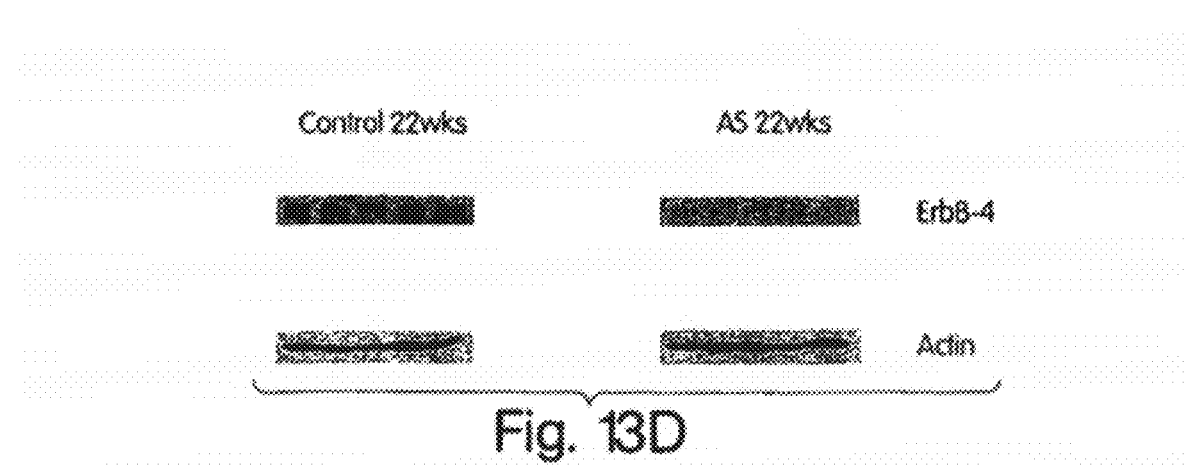

Western blotting using polyclonal antibodies for ErbB2 and ErbB4 was performed using protein samples derived from LV tissue of 6-week and 22-week aortic stenosis rats in comparison with age-matched controls (n=5 per group). FIGS. 13A and 13B show Western blots showing LV ErbB2 and β-actin protein levels in 6-week (FIG. 13A) aortic stenosis hearts and controls, and 22-week (FIG. 13B) aortic stenosis hearts and controls. FIGS. 13C and 13D show Western blots showing LV ErbB4 and β-actin protein levels in 6-week (FIG. 13C) aortic stenosis hearts and controls, and 22-week (FIG. 13D) aortic stenosis hearts and controls. Densitometric signals of each receptor were normalized to signals of β-actin. As shown in FIGS. 13A-13D and Table 2, ErbB2 and ErbB4 mRNA expression is preserved relative to controls in 6-weeks aortic stenosis animals at the stage of compensatory hypertrophy (NS) but ErbB2 (p<0.05) and ErbB4 (p<0.01) are downregulated in 22-week aortic stenosis animals during early failure. Thus, a decrease in both LV message and protein levels of ErbB2 and ErbB4 is present at the stage of early failure in this model of pressure overload.

In Situ Hybridization for Neuregulin

Antisense digoxigenin-labeled mRNA of neuregulin generated reproducible hybridization signals on LV cryosections, whereas the corresponding sense transcript generated no signal above background. Neuregulin signals in adult heart cryosections were observed in the endothelial cells of the cardiac microvasculature with minimal or no signal in other cell compartments. There was no difference between control and aortic stenosis animals.

Example IV

Inhibition of Heart Failure in Aortic Stenosis Mice by Polypeptides that Contain a Neuregulin-1 EGF-Like Domain The Examples above describe data showing that rhGGF2 suppresses apoptosis and stimulates cardiomyocyte hypertrophy in an ErbB2- and ErbB4-dependent fashion. Moreover, ErbB2 and ErbB4 receptors are down-regulated in the left ventricles of rats with pressure overload-induced heart failure. Cardiomyocyte apoptosis is extremely rare during the early compensatory hypertrophic stage in aortic stenosis mice (i.e., 4 weeks after aortic banding), but consistently appears during the transition to early heart failure (i.e., 7 weeks after aortic banding).

These above observations indicate that administration of polypeptides that have an EGF-like domain encoded by a neuregulin gene will be useful in inhibiting the progression of and/or protecting against congestive heart failure. While not wishing to be bound by theory, it is likely that neuregulin treatment will strengthen the pumping ability of the heart by stimulating cardiomyocyte hypertrophy, and partially or completely prevent further deterioration of the heart by suppressing cardiomyocyte apoptosis.

One of ordinary skill in the art can readily determine the optimal dosage regimen required for providing prophylaxis against congestive heart disease or for slowing or halting progression of already-existent heart disease, using one of the many animals models for congestive heart failure that are known in the art. For example, as a starting point, the relative efficacy of a 0.3 mg/kg dose of GGF2 administered at early stages and late stages of cardiac disease in the aortic stenosis mouse model may be assessed as follows.

Group 1 (n=6); treated: injections of rhGGF2 (0.3 mg/kg given on alternate days), initiated 48 hours after aortic banding and continued through week 7.

Group 2 (n=6); treated: injections of rhGGF2 (0.3 mg/kg given on alternate days), initiated at the beginning of week 4 after aortic banding and continued through week 7.

Group 3 (n=6); control: sham injections, initiated 48 hours after aortic banding and continued through week 7.

Group 4 (n=6); control: sham injections, initiated at the beginning of week 4 after aortic banding and continued through week 7.

Animals are sacrificed at the end of week 7. Prior to sacrifice, left ventricular hemodynamics are measured as described in Example I above, or using any standard protocol. Confocal microscopy may be used to quantitate myocyte growth (hypertrophy) and myocyte apoptosis by in situ nick-end labeling (TUNEL) or similar techniques for measuring cell death, using standard protocols or as described in Example 1.

One of skill in the art will fully comprehend and know how to perform the experiments needed to determine the optimal neuregulin dosage regimen (e.g., amount of dose, frequency of administration, optimal time during the disease course to initiate neuregulin treatment) for minimizing, preventing, or even reversing congestive heart disease.

Example V

NRG-1 Inhibits Anthracycline-Induced Apoptosis in Rat Cardiac Myocytes

The anthracycline antibiotics (e.g., daunorubicin, and doxorubicin) have been a mainstay of cancer chemotherapy for more than 20 years. However, the short- and long-term cardiotoxicity of these drugs limits both the individual dose and the cumulative dose that can be delivered to a patient.

There are two clinical types of anthracycline-induced cardiotoxicity. The acute type, which can occur after a single dose of anthracycline, is characterized by electrocardiographic changes, arrhythmias, and a reversible decrease in ventricular contractile function. The chronic, delayed type is characterized by a largely irreversible decrease in ventricular contractile function which progresses to dilated cardiomyopathy and congestive heart failure. The incidence of this chronic cardiotoxicity is in direct proportion to the cumulative anthracycline dose.

Figure 14:
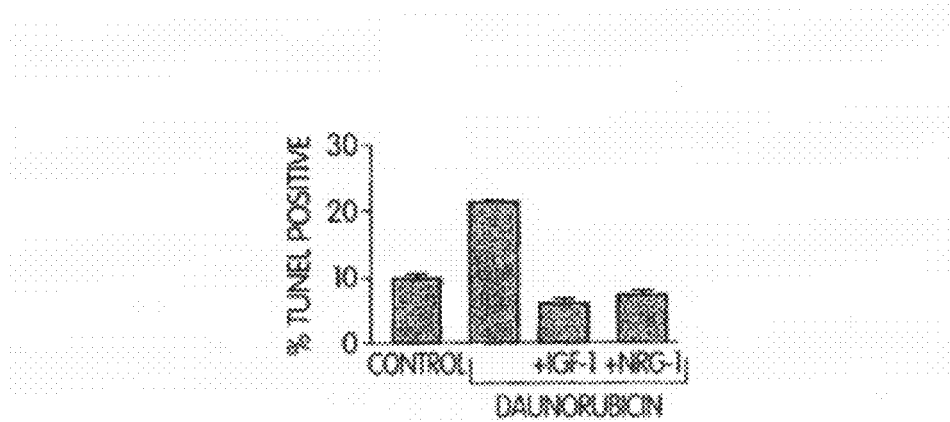
FIG. 14 is a graph showing that rat cardiomyocyte cultures pre-treated with IGF-1 or NRG-1 are less susceptible to daunorubicin-induced apoptosis.

We have found that GGF2 (NRG-1) inhibits anthracycline-induced apoptosis in rat cardiac myocytes. FIG. 14 shows that rat cardiomyocyte cultures pre-treated with IGF-1 or NRG-1 are less susceptible to apoptosis (indicated by TUNEL staining) induced by 1 μM daunorubicin. For IGF-1 this protective effect is rapid, and can be achieved within 30 minutes of pre-incubation, similar to what was reported for fetal cardiac myocytes. In contrast, this effect takes 24 hours of pre-incubation with NRG-1.

Figure 15A:
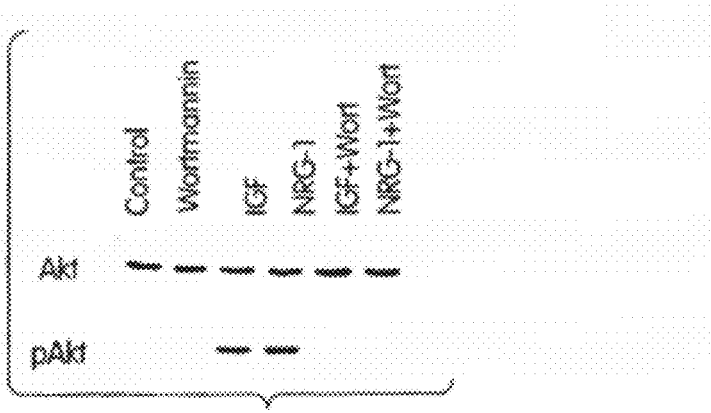
FIG. 15A is a representation of a phosphorylation assay showing that IGF- and NRG-1-stimulated phosphorylation of Akt is inhibited by the PI-3 kinase inhibitor wortmannin.
Figure 15B:
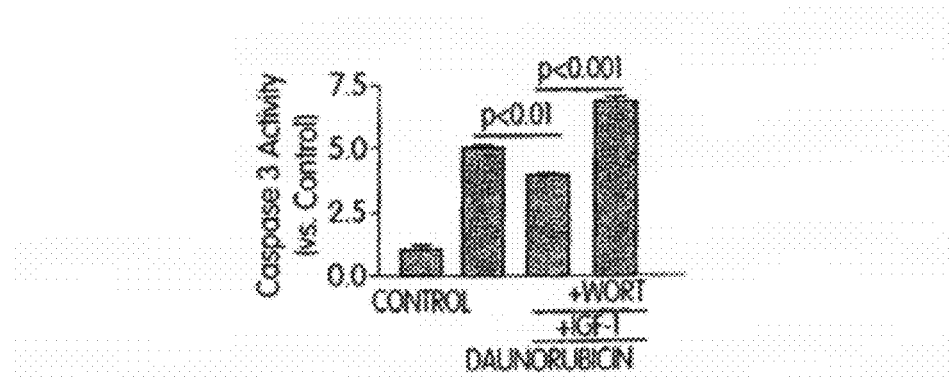
FIG. 15B is a graph showing that IGF-1 and NRG-1 inhibition of caspase 3 activation in cells exposed to daunorubicin is PI-3 kinase-dependent.

FIG. 15A shows that both IGF-1 and NRG-1 cause rapid phosphorylation of Akt (FIG. 15A), and that this is inhibited by the PI-3 kinase inhibitor wortmannin. Akt has been implicated in mediating survival signals in some systems through phosphorylation and inactivation of the pro-apoptotic protein caspase 3. Either thirty minutes of pre-incubation with IGF4 or 24 hours of pre-incubation with NRG-1 prevent anthracycline-induced activation of caspase 3. This effect, as well as the survival effect of IGF-1, is completely prevented by wortmannin (FIG. 15B). Thus, activation of PI-3 kinase is necessary for the cytoprotective effect of IGF on myocytes. However, the lack of cytoprotection by NRG-1 over the same time course indicates that activation of PI-3 kinase and Akt is not sufficient for cytoprotection. The relatively long NRG-1 exposure period needed for cytoprotection suggests that NRG-1-dependent protection of cardiomyocytes against apoptosis requires de novo protein synthesis. Consistent with this observation, treatment of the cells with cyclohexamide inhibits the anti-apoptotic effect of NRG-1 on cardiomyocytes.

The results described above show that NRG-1 effectively inhibits anthracycline-induced apoptosis. Therefore, NRG-1 could be used to limit or prevent cardiotoxicity in patients undergoing anthracycline chemotherapy and to treat patients have congestive heart failure caused by cardiotoxicity induced by anthracyclines or other cardiotoxic agents.

Existing in the art are various well known animal models of anthracycline-induced cardiotoxicity. Mouse, rat, rabbit, hamster, dog, swine, and monkey models for assessing the relative efficacy of therapeutic compounds for ameliorating anthracycline-induced cardiotoxicity are described in "Amelioration of Chemotherapy Induced Cardiotoxicity" Semin. Oncol. 25(4)Suppl. 10, August 1998 (see, e.g., Myers, Semin. Oncol. 25:10-14, 1998; Herman and Ferrans, Semin. Oncol. 25:15-21, 1998; and Imondi, Semin. Oncol. 25:22-30, 1998). These models may be used to determine the optimal neuregulin or neuregulin-like polypeptide treatment regimen (e.g., amount and frequency of dosage, and timing relative to anthracycline administration), for minimizing, preventing, or reversing anthracycline-induced cardiotocicity.

Example VI

Neuregulin-Dependent Inhibition of Cardiac Failure by Anthracycline/Anti-ErbB2 (Anti-HER2) Combination Therapy Various types of cancer cells display increased expression or increased biological activity of ErbB receptors. These transmembrane receptor tyrosine kinases bind growth factors belonging to the neuregulin (also known as heregulin) family. Expression of the ErbB2 receptor (also known as HER2 and neu) in cancer cells has been correlated with increases in proliferation of carcinoma cells derived from various tissues, including, but not limited to, breast, ovary, prostate, colon, pancreas, and salivary gland.

Recently, it has been shown that HERCEPTIN® (Trastuzumab; Genentech, Inc., South San Franciico, Calif.), a humanized monoclonal antibody that specifically binds the extracellular domain of the human ErbB2 (HER2) receptor, inhibits the growth of breast carcinoma cells in vitro and in vivo by down-regulating ErbB2 activity. A Phase III clinical trial evaluating the safety and efficacy of combining HERCEPTIN® therapy with traditional anthracycline (doxorubicin) chemotherapy in breast cancer patients showed that patients receiving the combination therapy displayed greater tumor shrinkage and inhibition of cancer progression than patients receiving either therapy alone. However, patients receiving combination therapy also suffered increased cardiotoxicity relative to patients receiving anthracycline therapy alone, indicating that anti-ErbB2 (anti-HER2) antibodies such as HERCEPTIN® increase anthracycline-induced cardiotoxicity. In addition, patients that had previously been treated with doxorubicin and later received HERCEPTIN® also showed an increased incidence of cardiotoxicity, relative to patients treated with doxorubicin alone.

Given the recently-shown success of HERCEPTIN® fanthracycline combination therapy in ameliorating ErbB2-overexpressing breast tumors, it is likely that similar combination therapies will soon be used to treat other ErbB2-overexpressing tumors. However, the benefit/risk ratio of anti-ErbB2 antibody/anthracycline combination therapy would be greatly improved if its associated cardiotoxicity could be decreased or prevented.

Animal models of anthracycline-induced cardiotoxicity (see, e.g., Herman and Ferrans, *Semin. Oncol.* 25:15-21, 1998 and Heitman et al. *Cancer Res.* 58:195-197, 1998) are well-known in the art. Moreover, antibodies that block neuregulin binding to ErbB2 receptors, such as those described above, are well-known. By inducing anthracycline/anti-ErbB2 antibody-dependent heart failure in known animal models for anthracycline toxicity, one of skill in the art will readily be able to determine the neuregulin dosage regimen required to minimize or prevent such heart failure.

Other Embodiments

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth, and follows in the scope of the appended claims.

What is claimed is:

1. A method for treating or preventing congestive heart failure in a mammal, said method comprising administering a polypeptide comprising an epidermal growth factor-like (ECG-like) domain to said mammal, wherein said EGF-like domain is encoded by a neuregulin gene, wherein said administering is in an amount effective to treat or prevent heart failure in said mammal.

2. The method of claim 1, wherein said neuregulin gene is the NRG-1 gene.

3. The method of claim 2, wherein said polypeptide is encoded by the NRG-1 gene.

4. The method of claim 3, wherein said polypeptide is recombinant human GGF2.

5. The method of claim 1, wherein said neuregulin gene is the NRG-2 gene.

6. The method of claim 5, wherein said polypeptide is encoded by the NRG-2 gene.

7. The method of claim 1, wherein said neuregulin gene is the NRG-3 gene.

8. The method of claim 7, wherein said polypeptide is encoded by the NRG-3 gene.

9. The method of claim 1, wherein said mammal is a human.

10. The method of claim 1, wherein said congestive heart failure results from hypertension; ischemic heart disease; exposure to a cardiotoxic compound; myocarditis; thyroid disease; viral infection; gingivitis; drug abuse; alcohol abuse; periocarditis; atherosclerosis; vascular disease; hypertrophic cardiomyopathy; myocardial infarction; left ventricular systolic dysfunction; coronary bypass surgery; starvation; an eating disorder; or a genetic defect.

11. The method of claim 10, wherein said mammal has undergone a myocardial infarction.

12. The method of claim 10, wherein said cardiotoxic compound is an anthracycline, alcohol, or cocaine.

13. The method of claim 12, wherein said anthracycline is doxorubicin or daunomycin.

14. The method of claim 12, wherein an anti-ErbB2 or anti-HER2 antibody is administered to said mammal before, during, or after anthracycline administration.

15. The method of claim 12, wherein said cardiotoxic compound is an anti-ErbB2 or anti-HER2 antibody.

16. The method of claim 14 or 15, wherein said anti-ErbB2 or anti-HER2 antibody is HERCEPTINO.

17. The method of claim 12, wherein said polypeptide is administered prior to exposure to said cardiotoxic compound.

18. The method of claim 12, wherein said polypeptide is administered during exposure to said cardiotoxic compound.

19. The method of claim 12, wherein said polypeptide is administered after exposure to said cardiotoxic compound.

20. The method of claim 1, wherein said polypeptide is administered prior to the diagnosis of congestive heart failure in said mammal.

21. The method of claim 1, wherein said polypeptide is administered after the diagnosis of congestive heart failure in said mammal.

22. The method of claim 1, wherein said polypeptide is administered to a mammal that has undergone compensatory cardiac hypertrophy.

23. The method of claim 1, wherein administration of said polypeptide maintains left ventricular hypertrophy.

24. The method of claim 1, wherein said method prevents progression of myocardial thinning.

25. The method of claim 1, wherein administration of said polypeptide inhibits cardiomyocyte apoptosis.

26. The method of claim 1, wherein said polypeptide is administered by administering an expression vector encoding said polypeptide to said mammal.

* * * * *

UNITED STATES PATENT AND TRADEMARK OFFICE
CERTIFICATE OF CORRECTION

| | |
|---|---|
| PATENT NO. | : 8,394,761 B2 |
| APPLICATION NO. | : 13/292193 |
| DATED | : March 12, 2013 |
| INVENTOR(S) | : Mark Marchionni et al. |

It is certified that error appears in the above-identified patent and that said Letters Patent is hereby corrected as shown below:

In the Claims:

At column 40, claim number 16, line number 52, the word "HERCEPTINO" should be deleted and replaced with the word "HERCEPTIN®".

Signed and Sealed this
Eighteenth Day of June, 2013

Teresa Stanek Rea
*Acting Director of the United States Patent and Trademark Office*